US010004751B2

(12) United States Patent
Ott et al.

(10) Patent No.: US 10,004,751 B2
(45) Date of Patent: Jun. 26, 2018

(54) COMPOSITIONS AND METHODS FOR TREATING DENGUE VIRUS INFECTION

(71) Applicants: The J. David Gladstone Institutes, San Francisco, CA (US); The Regents of the University of California, Oakland, CA (US)

(72) Inventors: Melanie Ott, Mill Valley, CA (US); Andrew S. Kondratowicz, San Francisco, CA (US); Nevan John Krogan, San Francisco, CA (US); Priya Shirish Shah, San Francisco, CA (US); Krystal Ann Fontaine, San Francisco, CA (US)

(73) Assignees: The J. David Gladstone Institutes, San Francisco, CA (US); The Regents of the University of California, Oakland, CA (US)

(*) Notice: Subject to any disclaimer, the term of this patent is extended or adjusted under 35 U.S.C. 154(b) by 0 days. days.

(21) Appl. No.: 15/324,561

(22) PCT Filed: Jul. 7, 2015

(86) PCT No.: PCT/US2015/039424
§ 371 (c)(1),
(2) Date: Jan. 6, 2017

(87) PCT Pub. No.: WO2016/007540
PCT Pub. Date: Jan. 14, 2016

(65) Prior Publication Data
US 2017/0209460 A1 Jul. 27, 2017

Related U.S. Application Data

(60) Provisional application No. 62/022,891, filed on Jul. 10, 2014.

(51) Int. Cl.
| | | |
|---|---|---|
| A61K 31/5513 | (2006.01) | |
| A61K 9/00 | (2006.01) | |
| A61K 31/5377 | (2006.01) | |
| A61K 31/506 | (2006.01) | |
| A61K 31/444 | (2006.01) | |

(52) U.S. Cl.
CPC ........ *A61K 31/5513* (2013.01); *A61K 9/0019* (2013.01); *A61K 9/0053* (2013.01); *A61K 31/444* (2013.01); *A61K 31/506* (2013.01); *A61K 31/5377* (2013.01)

(58) Field of Classification Search
None
See application file for complete search history.

(56) References Cited

U.S. PATENT DOCUMENTS

| | | |
|---|---|---|
| 3,547,119 A | 12/1970 | Hall et al. |
| 4,311,137 A | 1/1982 | Gerard |
| 4,531,937 A | 7/1985 | Yates |
| 4,755,173 A | 7/1988 | Konopka et al. |
| 6,017,328 A | 1/2000 | Fischell et al. |
| 8,404,677 B2 | 3/2013 | Kim et al. |
| 8,409,809 B2 | 4/2013 | Meitinger et al. |
| 8,629,132 B2 | 1/2014 | Lee et al. |
| 8,669,091 B2 | 3/2014 | Gentschev et al. |
| 2012/0040961 A1 | 2/2012 | Gray et al. |
| 2012/0329780 A1 | 12/2012 | Thormann et al. |
| 2012/0329785 A1 | 12/2012 | Thormann et al. |
| 2013/0157999 A1 | 6/2013 | Baker-Glenn et al. |
| 2013/0158032 A1 | 6/2013 | Baker-Glenn et al. |
| 2013/0178429 A1 | 7/2013 | Liu et al. |
| 2013/0225584 A1 | 8/2013 | Andreotti et al. |
| 2013/0296317 A1 | 11/2013 | McCauley et al. |
| 2013/0338106 A1 | 12/2013 | McCauley et al. |
| 2014/0005183 A1 | 1/2014 | Galatsis et al. |
| 2014/0107141 A1 | 4/2014 | Wagner et al. |

FOREIGN PATENT DOCUMENTS

| | | |
|---|---|---|
| WO | WO 2002100851 | 12/2002 |
| WO | 2012058193 | 3/2012 |
| WO | 2012143144 | 10/2012 |
| WO | 2012178015 | 12/2012 |
| WO | 2013046029 | 4/2013 |
| WO | 2013079494 | 6/2013 |
| WO | 2013079505 | 6/2013 |
| WO | 2014060112 | 4/2014 |
| WO | 2014060113 | 4/2014 |
| WO | WO 2014079709 | 5/2014 |

OTHER PUBLICATIONS

Chen, et al. (2012) "Discovery of Selective LRRK2 Inhibitors Guided by Computational Analysis and Molecular Modeling"; J Med Chem. 55(11); pp. 5536-5545.

Deng et al. (2011) "Characterization of a selective inhibitor of the Parkinson's disease kinase LRRK2"; Nat Chem Biol. 7(4); pp. 203-205.

Gardet, A. et al. (2010) "LRRK2 is involved in the IFN-gamma response and host response to pathogens"; J Immunol. 185(9); pp. 5577-5585.

Hakimi, M. et al. (2011) "Parkinson's disease-linked LRRK2 is expressed in circulating and tissue immune cells and upregulated following recognition of microbial structures"; J Neural Transm (Vienna), 118(5); pp. 795-808.

Kavanagh, et al. (2013) "The development of CNS-active LRRK2 inhibitors using property-directed optimization"; Bioorg Med Chem Lett. 23(13); pp. 3690-3696.

(Continued)

*Primary Examiner* — Heidi Reese
(74) *Attorney, Agent, or Firm* — Michael B. Rubin; Bozicevic, Field & Francis LLP

(57) ABSTRACT

The present disclosure provides methods of treating a flavivirus infection, and compositions for use in the methods.

13 Claims, 8 Drawing Sheets

(56) References Cited

OTHER PUBLICATIONS

Kramer et al. (2012) "Small Molecule Kinase Inhibitors for LRRK2 and Their Application to Parkinson's Disease Models"; ACS Chem Neurosci. 3(3); pp. 151-160.

Lee et al.(2010) "Inhibitors of leucine-rich repeat kinase-2 protect against models of Parkinson's disease"; Nat Med. 16 (9); pp. 998-1000.

Li Tianxia, et al. (2014) "Novel LRRK2 GTP-binding inhibitors reduced degeneration in Parkinson's disease cell and mouse models"; Hum Mol Genet. 23(23); pp. 6212-6222.

Li Tianxia, et al (2015) "A novel GTP-binding inhibitor, FX2149, attenuates LRRK2 toxicity in Parkinson's disease models"; PLoS One 10(3):e0122461; pp. 1-15.

Marker et al. (2012) "LRRK2 kinase inhibition prevents pathological microglial phagocytosis in response to HIV-1 Tal protein"; J Neuroinflammation 9:261; pp. 1-12.

Stafa, et al. (2012) "GTPase activity and neuronal toxicity of Parkinson's disease-associated LRRK2 is regulated by ArfGAP1"; PLoS Genet. 8(2):e1002526.

Taymans, et al. (2011) "LRRK2 kinase activity is dependent on LRRK2 GTP binding capacity but independent of LRRK2 GTP binding"; PLoS One 6(8):e23207.

Vancraenenbroeck, et al. (2014) "In silico, in vitro and cellular analysis with a kinome-wide inhibitor panel correlates cellular LRRK2 dephosphorylation to inhibitor activity on LRRK2"; Front Mol Neurosci. vol. 7, art.51; pp. 1-19.

Xiong, Y. et al (2012) "ArfGAP1 is a GTPase activating protein for LRRK2: reciprocal regulation of ArfGAP1 by LRRK2"; J Neurosci. 32(11): pp. 3877-3886.

Zhang, et al. (2007) "Small-molecule synergist of the Wnt/beta-catenin signaling pathway"; Proc Natl Acad Sci U S A. 104(18); pp. 7444-7448.

Kim, et al "Discovery and Evaluation of Highly Selective and Orally Bioavailable Potent Inhibitors of LRRK2"; LRRK2 inhibitors Genosco; P024; 1 page; Downloaded on Jun. 13, 2014.

Fusco, et al (2014) " Review of Current Dengue Treatment and Therapeutics in Development"; *Journal of Bioanal Ysis & Biomedicine*, vol. S8; pp. 1-10.

FIG. 5A

LRRK2 – *Homo sapiens*
GenBank AAV63975

```
   1  masgscqgce edeetlkkli vrlnnvqegk qietlvqile dllvftyseh asklfqgkni
  61  hvpllivlds ymrvasvqqv gwsllcklie vcpgtmqslm gpqdvgndwe vlgvhqlilk
 121  mltvhnasvn lsviglktld llltsgkitl lildeesdif mlifdamhsf pandevqklg
 181  ckalhvlfer vseeqltefv enkdymills astnfkdeee ivlhvlhclh slaipcnnve
 241  vlmsgnvrcy nivveamkaf pmseriqevs ccllhrltlg nffnilvlne vhefvvkavq
 301  qypenaalqi salsclallt etiflnqdle eknenqendd egeedklfwl eacykaltwh
 361  rknkhvqeaa cwalnnllmy qnslhekigd edghfpahre vmlsmlmhss skevfqasan
 421  alstlleqnv nfrkillskg ihlnvlelmq khihspevae sgckmlnhlf egsntsldim
 481  aavvpkiltv mkrhetslpv qlealrailh fivpgmpees redtefhhkl nmvkkqcfkn
 541  dihklvlaal nrfignpgiq kcglkvissi vhfpdaleml slegamdsvl htlqmypddq
 601  eiqclglsli gylitkknvf igtghllaki lvsslyrfkd vaeiqtkgfq tilailklsa
 661  sfskllvhhs fdlvifhqms snimeqkdqq flnlcckcfa kvamddylkn vmleracdqn
 721  nsimveclll lgadanqake gsslicqvce kesspklvel llnsgsreqd vrkaltisig
 781  kgdsqiisll lrrlaldvan nsiclggfci gkvepswlgp lfpdktsnlr kqtniastla
 841  rmviryqmks aveegtasgs dgnfsedvls kfdewtfipd ssmdsvfaqs ddldsegseg
 901  sflvkkksns isvgefyrda vlqrcspnlq rhsnslgpif dhedllkrkr kilssddslr
 961  ssklqshmrh sdsisslase reyitsldls anelrdidal sqkccisvhl ehleklelhq
1021  naltsfpqql cetlkslthl dlhsnkftsf psyllkmsci anldvsrndi gpsvvldptv
1081  kcptlkqfnl synqlsfvpe nltdvvekle qlilegnkis gicsplrlke lkilnlsknh
1141  isslsenfle acpkvesfsa rmnflaampf lppsmtilkl sqnkfscipe ailnlphlrs
1201  ldmssndiqy lpgpahwksl nlrellfshn qisildlsek aylwsrvekl hlshnklkei
1261  ppeigclenl tsldvsynle lrsfpnemgk lskiwdlpld elhlnfdfkh igckakdiir
1321  flqqrlkkav pynrmklmiv gntgsgkttl lqqlmktkks dlgmqsatvg idvkdwpiqi
1381  rdkrkrdlvl nvwdfagree fysthphfmt qralylavyd lskgqaevda mkpwlfnika
1441  rasspvilv gthldvsdek qrkacmskit kellnkrgfp airdyhfvna teesdalakl
1501  rktiinesln fkirdqlvvg qlipdcyvel ekiilserkn vpiefpvidr krllqlvren
1561  qlqldenelp havhflnesg vlihfqdpal qlsdlyfvep kwlckimaqi ltvkvegcpk
1621  hpkgiisrrd vekflskkrk fpknymsqyf kllekfqial pigeeyllvp sslsdhrpvi
1681  elphcensei iirlyempyf pmgfwsrlin rlleispyml sgreralrpn rmywrqgiyl
1741  nwspeayclv gsevldnhpe sflkitvpsc rkgcilligqv vdhidslmee wfpglleidi
```

FIG. 5B

```
1801 cgegetllkk walysfndge ehqkillddl mkkaeegdll vnpdqprlti pisqiapdli
1861 ladlprniml nndelefeqa pefllgdgsf gsvyraayeg eevavkifnk htslrllrqe
1921 lvvlchlhhp slisllaagi rprmlvmela skgsldrllq qdkasltrtl qhrialhvad
1981 glrylhsami iyrdlkphnv llftlypnaa iiakiadygi aqyccrmgik tsegtpgfra
2041 pevargnviy nqqadvysfg lllydilttg griveglkfp nefdeleiqg klpdpvkeyg
2101 capwpmvekl ikqclkenpq erptsaqvfd ilnsaelvcl trrillpknv ivecmvathh
2161 nsrnasiwlg cghtdrgqls fldintegyt seevadsril clalvhlpve keswivsgtq
2221 sgtllvinte dgkkrhtlek mtdsvtclyc nsfskqskqk nfllvgtadg klaifedktv
2281 klkgaaplki lnignvstpl mclsestnst ernvmwggcg tkifsfsndf tiqklietrt
2341 sqlfsyaafs dsniitvvvd talyiakqns pvvevwdkkt eklcglidcv hflrevmvke
2401 nkeskhkmsy sgrvktlclq kntalwigtg gghilldls trrlirviyn fcnsvrvmmt
2461 aqlgslknvm lvlgynrknt egtqkqkeiq scltvwdinl phevqnlekh ievrkelaek
2521 mrrtsve (SEQ ID NO://)
```

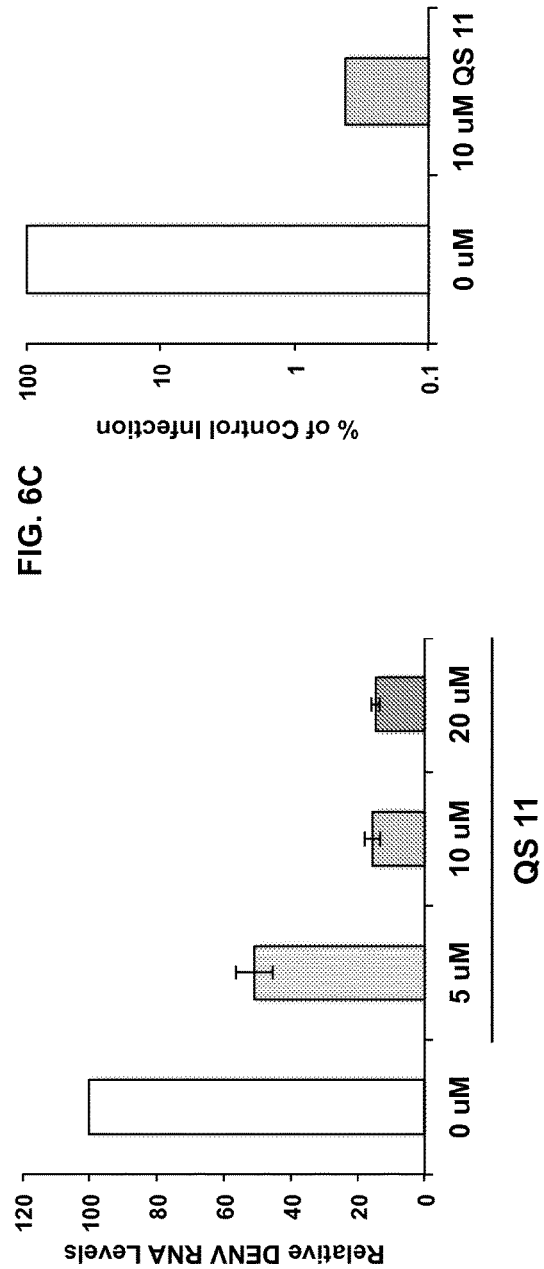
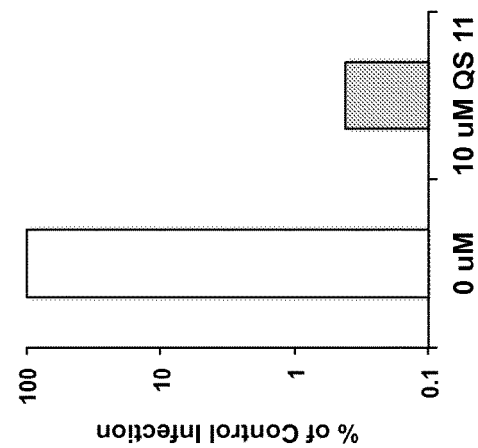
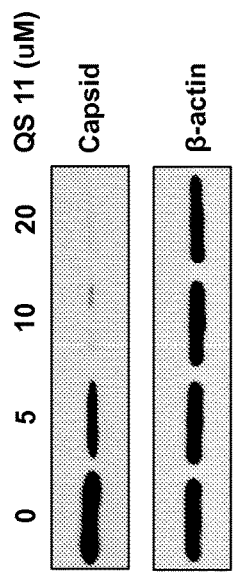
FIG. 6A
FIG. 6B
FIG. 6C

FIG. 7

```
  1 mgdpskqdil tifkrlrsvp tnkvcfdcga knpswasity gvflcidcsg shrslgvhls
 61 firsteldsn wswfqlrcmq vggnasassf fhqhgcstnd tnakynsraa qlyrekiksl
121 asqatrkhgt dlwldscvvp plspppkeed ffashvspev sdtawasaia epssltsrpv
181 ettlennegg qeqgpsvegl nvptkatlev ssiikkkpnq akkglgakkg slgaqklant
241 cfneiekqaq aadkmkeqed lakvvskees ivsslrlayk dleiqmkkde kmnisgkknv
301 dsdrlgmgfg ncrsvishsv tsdmqtieqe spimakprkk ynddsdddsyf tsssryfdep
361 velrsssfss wddssdsywk ketskdtetv lkttgysdrp tarrkpdyep ventdeaqkk
421 fgnvkaissd myfgrqsqad yetrarlerl sasssissad lfeeprkqpa gnyslssvlp
481 napdmaqfkq gvrsvagkls vfangvvtsi qdrygs
```

COMPOSITIONS AND METHODS FOR TREATING DENGUE VIRUS INFECTION

CROSS-REFERENCE

This application is a 35 U.S.C. § 371 national stage entry of International Application No. PCT/US15/39424, filed Jul. 7, 2015, which application claims the benefit of U.S. Provisional Patent Application No. 62/022,891, filed Jul. 10, 2014, which applications are incorporated herein by reference in their entireties.

INTRODUCTION

The genus flavivirus comprises about 70 viruses including major pathogens responsible for high rates of morbidity and mortality in animals and humans, such as Dengue virus, West Nile virus, Tick-borne Encephalitis virus, Japanese encephalitis virus, Yellow fever virus, virus of St. Louis encephalitis and Murray Valley virus.

Among flavivirus, Dengue virus is one of the major health problems worldwide, especially in tropical and sub-tropical regions. Dengue virus is grouped into four serotypes: DEN1, DEN2, DEN3 and DEN4 and is transmitted to humans by vectors, mainly the *Aedes aegypti* mosquito. The patient infected with Dengue virus may be asymptomatic or symptomatic, with clinical symptoms such as undifferentiated fever (UF), dengue fever (DF) and two more severe and occasionally fatal forms, called dengue hemorrhagic fever (DHF) and dengue shock syndrome (DSS).

There is a need for treatments for flavivirus infection, including Dengue virus infection.

SUMMARY

The present disclosure provides methods of treating a flavivirus infection, and compositions for use in the methods.

BRIEF DESCRIPTION OF THE DRAWINGS

FIG. 5A-5B provide an amino acid sequence of an LRRK2 polypeptide (SEQ ID NO: 1).

FIG. 6A-6C depict the effect of an ARFGAP1 inhibitor on DENV replication.

FIG. 7 provides an amino acid sequence of an ARFGAP1 polypeptide (SEQ ID NO:2).

DEFINITIONS

Definitions of Selected Chemical Terminology

Figure 1:
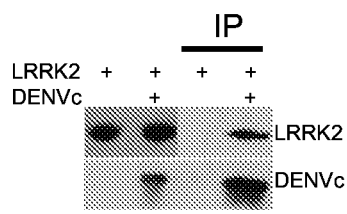
FIG. 1 depicts interaction of Dengue virus (DENV) capsid with leucine-rich repeat kinase 2 (LRRK2).

The nomenclature of certain compounds or substituents are used in their conventional sense, such as described in chemistry literature including but not limited to Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$ where R$^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —$C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group is specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —$NR^{37}R^{38}$—, =N—N=, —N=N—, —N=N—$NR^{39}R^{40}$, —$PR^{41}$, —$P(O)_2$—, —$POR^{42}$—, —O—$P(O)_2$—, —S—O—, —S—(O)—, —$SO_2$—, —$SnR^{43}R^{44}$— and the like, where $R^{37}$, $R^{38}$, $R^{39}$, $R^{40}$, $R^{41}$, $R^{42}$, $R^{43}$ and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(O$^-$, R$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Additional Definitions

The term "flavivirus" refers to any of the following viruses: Dengue virus serotype 1 (DEN1), Dengue virus serotype 2 (DEN2), Dengue virus serotype 3 (DEN3), Dengue virus serotype 4 (DEN4), West Nile virus (WNV), St. Louis Encephalitis virus, Japanese Encephalitis virus, Yellow Fever virus, Kunjin virus, Kyasanur Forest Disease virus, Tick-borne Encephalitis virus (TBEV), Murray Valley virus, LANGAT virus, Louping disease virus and Powassan virus and Omsk hemorrhagic fever virus, including in general, all viruses with 70% identity over the entire viral genome with respect to above-mentioned viruses.

"Dengue virus" refers to any serotype of Dengue virus, including Dengue virus serotype 1 (DEN1), Dengue virus serotype 2 (DEN2), Dengue virus serotype 3 (DEN3), Dengue virus serotype 4 (DEN4).

The terms "patient" and "subject" and "individual" are used interchangeably herein and include any mammal. Mammals include, e.g., humans, experimental animals including rats, mice, and guinea pigs, domestic and farm animals, and zoo, sports, or pet animals, such as dogs, horses, cats, cows, and the like. In some cases, the individual is a human.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to flavivirus infection (e.g., Dengue virus infection) is contemplated. By "treatment" is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a parameter or symptom associated with a flavivirus infection. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

"LRRK2," as used herein, refers to a polypeptide having at least 85%, at least 90%, at least 95%, at least 98%, at least 99%, or 100%, amino acid sequence identity to a contiguous stretch of from 1000 amino acids to about 1500 amino acids, from about 1500 amino acids to about 2000 amino acids, from about 2000 amino acids to about 2500 amino acids, or from 2500 amino acids to 2527 amino acids, of the amino acid sequence depicted in FIG. 5A-5B. "LRRK2" includes a polypeptide having 100% amino acid sequence identity to the amino acid sequence depicted in FIG. 5A-5B, and also includes naturally-occurring allelic variants of the amino acid sequence depicted in FIG. 5A-5B.

"ARFGAP1," as used herein refers to a polypeptide having at least 85%, at least 90%, at least 95%, at least 98%, at least 99%, or 100%, amino acid sequence identity to a contiguous stretch of from 100 amino acids to 200 amino acids, from 200 amino acids to 300 amino acids, from 300 amino acids to 400 amino acids, or from 400 amino acids to 516 amino acids, of the amino acid sequence depicted in FIG. 7. "ARFGAP1" includes a polypeptide having 100% amino acid sequence identity to the amino acid sequence depicted in FIG. 7, and also includes naturally-occurring allelic variants of the amino acid sequence depicted in FIG. 7.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an LRRK2 inhibitor" includes a plurality of such inhibitors and reference to "the formulation" includes reference to one or more formulations and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of treating a flavivirus infection, and compositions for use in the methods.

Treatment Methods

The present disclosure provides methods of treating a flavivirus infection. A subject treatment method comprises administering to an individual in need thereof an effective amount of an LRRK2 inhibitor. In some cases, the LRRK2 inhibitor is an agent that inhibits kinase activity of LRRK2. In some cases, the LRRK2 inhibitor is an agent that inhibits GTPase activity of LRRK2. In some cases, the LRRK2 inhibitor inhibits the activity of ARFGAP1, a protein that activates GTPase activity of LRRK2.

As shown in the Examples, Dengue virus (DENV) interacts with leucine-rich repeat kinase 2 (LRRK2). Also as shown in the Examples, an LRRK2 inhibitor inhibits DENV infection and reduces DENV viral genome abundance, in both a lung cancer cell line and in primary human hepatocytes.

In some cases, an "effective amount" of an LRRK2 inhibitor is an amount that, when administered to an individual in need thereof in monotherapy or in combination therapy with at least a second therapeutic agent, is effective to reduce the number of genome copies of a flavivirus in the individual. For example, in some cases, an "effective amount" of an LRRK2 inhibitor is an amount that, when administered to an individual in need thereof in monotherapy or in combination therapy with at least a second therapeutic agent, is effective to reduce the number of genome copies of a flavivirus in the individual by at least about 25%, at least about 50%, at least about 75%, or more than 75%, compared to the number of genome copies of the flavivirus in the absence of treatment with the LRRK2 inhibitor. In some cases, an "effective amount" of an LRRK2 inhibitor is an amount that, when administered to an individual in need thereof in monotherapy or in combination therapy with at least a second therapeutic agent, is effective to reduce the number of genome copies of a dengue virus in the individual by at least about 25%, at least about 50%, at least about 75%, or more than 75%, compared to the number of genome copies of the dengue virus in the absence of treatment with the LRRK2 inhibitor. In some cases, an "effective amount" of an LRRK2 inhibitor is an amount that, when administered to an individual in need thereof in monotherapy or in combination therapy with at least a second therapeutic agent, is effective to reduce the number of genome copies of a flavivirus to less than 100 genome copies/mL serum. In some cases, an "effective amount" of an LRRK2 inhibitor is an amount that, when administered to an individual in need thereof in monotherapy or in combination therapy with at least a second therapeutic agent, is effective to reduce the number of genome copies of a dengue virus to less than 100 genome copies/mL serum.

In some cases, an "effective amount" of an LRRK2 inhibitor is an amount that, when administered to an individual in need thereof in monotherapy or in combination therapy with at least a second therapeutic agent, is effective to achieve a reduction in viral titer of flavivirus in the individual. For example, in some cases, an "effective amount" of an LRRK2 inhibitor is an amount that, when administered to an individual in need thereof in monotherapy or in combination therapy with at least a second therapeutic agent, is effective to achieve a reduction in flavivirus viral titer in the serum of the subject in the range of about 1.5-log to about a 2.5-log reduction, about a 3-log to about a 4-log reduction, or a greater than about 5-log reduction compared to the viral load before administration of the LRRK2 inhibitor (as monotherapy or in combination therapy). In some cases, an "effective amount" of an LRRK2 inhibitor is an amount that, when administered to an individual in need thereof in monotherapy or in combination therapy with at least a second therapeutic agent, is effective to achieve a reduction in Dengue virus viral titer in the serum of the subject in the range of about 1.5-log to about a 2.5-log reduction, about a 3-log to about a 4-log reduction, or a greater than about 5-log reduction compared to the viral load before administration of the LRRK2 inhibitor (as monotherapy or in combination therapy).

In some cases, an "effective amount" of an LRRK2 inhibitor is an amount that, when administered to an individual in need thereof in monotherapy or in combination therapy with at least a second therapeutic agent, is effective to reduce flavivirus viral titers to undetectable levels. In some cases, an "effective amount" of an LRRK2 inhibitor is an amount that, when administered to an individual in need thereof in monotherapy or in combination therapy with at least a second therapeutic agent, is effective to reduce Dengue virus viral titers to undetectable levels.

In some cases, an "effective amount" of an LRRK2 inhibitor is an amount that, when administered to an individual in need thereof in monotherapy or in combination therapy with at least a second therapeutic agent, is effective to achieve at least a 25%, a 30%, a 35%, a 40%, a 50%, a 60%, a 70%, an 80%, a 90%, or a greater than 90%, reduction in the replication of flavivirus in the individual, compared to pre-treatment replication levels in the individual. In some cases, an "effective amount" of an LRRK2 inhibitor is an amount that, when administered to an individual in need thereof in monotherapy or in combination therapy with at least a second therapeutic agent, is effective to achieve at least a 25%, a 30%, a 35%, a 40%, a 50%, a 60%, a 70%, an 80%, a 90%, or a greater than 90%, reduction in the replication of Dengue virus in the individual, compared to pre-treatment replication levels in the individual.

In some cases, an "effective amount" of an LRRK2 inhibitor is an amount that, when administered to an individual in need thereof in monotherapy or in combination therapy with at least a second therapeutic agent, is effective to ameliorate a symptom of a flavivirus infection, e.g., to ameliorate a symptom of a Dengue virus infection.

Whether a subject treatment method is effective in treating a flavivirus (e.g., Dengue virus) infection can be determined using any of a variety of well-known methods. Methods for determining effectiveness of treatment for a Dengue virus infection are known in the art and are described below.

Diagnosis and Detection Methods

DENV can be detected in a blood or blood fraction (e.g., serum) from an individual. For example, a blood sample, a blood fraction sample, or other sample (e.g., CSF) can be obtained within the first 5 days of the appearance of symptoms; and the blood or blood fraction sample can be tested for DENV. A sample can be obtained from an individual after the appearance of symptoms (e.g., one week or more than one week); and the sample can be tested for DENV. Reverse transcription-polymerase chain reaction (RT-PCR) can be used to detect DENV genomes in a sample obtained from an individual. RT-PCR suitable for use includes one-step RT-PCR, real-time RT-PCR, and nested PCR. See, e.g., U.S. Patent Publication No. 2013/0130235 for methods of detecting DENV in a sample using PCR.

Antibody to DENV can be detected in a sample (e.g., blood, serum, plasma, etc.) obtained from an individual. IgM or IgG specific for DENV can be detected. For example, seroconversion from negative to positive of IgM specific for DENV can be used to detect DENV infection. An IgM capture enzyme-linked immunosorbent assay (MAC-ELISA) can be used to detect the presence in a sample of IgM specific for DENV; and to make a diagnosis of DENV.

An enzyme-linked immunosorbent assay (ELISA) can be used to detect the presence, and/or measure the level of, IgG specific for DENV in a sample (e.g., blood, serum, plasma, etc.) obtained from an individual.

The non-structural protein 1 (NS1) of DENV can be used to detect a DENV infection. Dengue NS1 can be detected in the serum of DENV infected individuals as early as 1 day post onset of symptoms (DPO), and up to 18 days DPO. An ELISA can be used to detect Dengue NS1. See, e.g., U.S. Patent Publication No. 2014/0051067 for methods of detecting Dengue NS1 in a sample obtained from an individual.

A plaque reduction and neutralization test (PRNT) can be used to detect the presence and/or level of antibody to DENV. Serum from an individual is contacted with an uninfected cell (a cell not infected with DENV) in vitro, forming a serum/uninfected cell sample. The serum/uninfected cell sample is contacted with DENV. The ability of the serum to inhibit infection of the uninfected cell by the DENV is an indication of the presence of neutralizing anti-DENV antibodies in the serum. Infection of the cell by DENV is indicated by plaque formation.

LRRK2 Inhibitors

In some cases, a suitable LRRK2 inhibitor is an agent that inhibits LRRK2 kinase activity. For example, in some cases, a suitable LRRK2 inhibitor is an agent that inhibits LRRK2 kinase activity by at least 10%, at least 15%, at least 20%, at least 25%, at least 30%, at least 40%, at least 50%, at least 60%, at least 70%, at least 80%, at least 90%, or more than 90%, compared to the level of kinase activity in the absence of the agent.

LRRK2 inhibitors that are suitable for use in a subject treatment method include, but are not limited to, a compound of the formula (I):

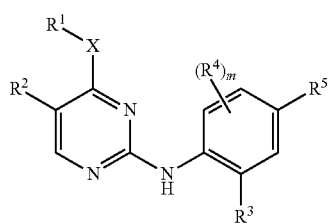

Formula (I)

wherein:
m is from 0 to 3;
X is: $-NR^a-$; $-O-$; or $-S(O)_r-$ wherein r is from 0 to 2 and $R^a$ is hydrogen or $C_{1-6}$alkyl;
$R^1$ is: $C_{1-6}$alkyl; $C_{1-6}$alkenyl; $C_{1-6}$ alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$ alkyl; tetrahydrofuranyl; tetrahydrofuranyl-$C_{1-6}$ alkyl; oxetanyl; or oxetan-$C_{1-6}$ alkyl;

or $R^1$ and $R^a$ together with the atoms to which they are attached may form a three to six membered ring that may optionally include an additional heteroatom selected from O, N and S, and which is substituted with oxo, halo or $C_{1-6}$alkyl;

$R^2$ is: halo; $C_{1-6}$alkoxy; cyano; $C_{1-6}$alkynyl; $C_{1-6}$alkenyl; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$ alkyl;

or $R^1$ and $R^2$ together with the atoms to which they are attached may form a three to six membered ring that may optionally include an additional heteroatom selected from O, N and S, and which is substituted with oxo, halo or $C_{1-6}$alkyl;

$R^3$ and $R^4$ each independently is: halo; $C_{1-6}$alkyl; $C_{1-6}$alkoxy; $C_{3-6}$cycloalkyloxy; halo-$C_{1-6}$alkyl; or halo-$C_{1-6}$alkoxy;

or $R^3$ and $R^4$ together with the atoms to which they are attached may form a five- or six-membered ring that optionally includes one or two heteroatoms each independently selected from O, N and S, the ring being optionally substituted one or more times with $R^6$;

$R^5$ is: $C_{1-6}$alkyl-sulfonyl; $C_{3-6}$cycloalkylsulfonyl; $C_{3-6}$cycloalkyl-$C_{1-6}$ alkylsulfonyl; cyano; cyano-$C_{1-6}$alkyl; heterocyclyl optionally substituted one or more times with $R^6$; carbonyl-heterocyclyl; heterocyclyl-$C_{1-6}$alkyl wherein the heterocyclyl moiety is optionally substituted one or more times with $R^6$; halo-$C_{1-6}$alkyl; heterocyclyl-sulfonyl wherein the heterocyclyl moiety is optionally substituted one or more times with $R^6$; or carboxy; and $R^6$ is: $C_{1-6}$ alkyl; halo; halo-$C_{1-6}$ alkyl; or oxo.

For example, the LRRK2 inhibitor may be a compound of the Formula (I):

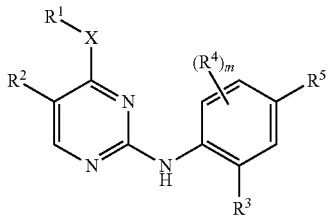

Formula (I)

wherein:
m is from 0 to 3;
X is: $-NR^a$; $-O-$; or $-S(O)_r-$ wherein r is from 0 to 2 and $R^a$ is hydrogen or $C_{1-6}$alkyl;
$R^1$ and $R^a$ together with the atoms to which they are attached may form a three to six membered ring that may optionally include an additional heteroatom selected from O, N and S, and which may be optionally substituted with oxo, halo or $C_{1-6}$alkyl. In certain embodiments of formula I, $R^1$ and $R^a$ together with the atoms to which they are attached form a five or six membered ring. In certain embodiments, $R^1$ and $R^a$ together with the atoms to which they are attached form a pyrolidinyl, piperidinyl or oxazoladinonyl group.

In certain embodiments, $R^2$ is acetyl. In certain embodiments of formula I, when $R^1$ is cyclopropyl, cyclobutyl, cyclopropyl-$C_{1-6}$alkyl or cyclobutyl-$C_{1-6}$alkyl, then X is —O—.

In certain embodiments of formula I, m is from 0 to 2. In certain embodiments of formula I, m is 0 or 1. In certain embodiments of formula I, m is 0. In certain embodiments of formula I, m is 1. In certain embodiments of formula I, r is 0. In certain embodiments of formula I, r is 2. In certain embodiments of formula I, X is —$NR^a$— or —O—. In certain embodiments of formula I, X is —$NR^a$. In certain embodiments of formula I, X is —O—. In certain embodiments of formula I, X is —$S(O)_n$—. In certain embodiments of formula I, X is —NH— or —O—. In certain embodiments of formula I, $R^a$ is hydrogen. In certain embodiments of formula I, $R^a$ is $C_{1-6}$alkyl. In certain embodiments of formula I, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; $C_{3-6}$cycloalkyl; or $C_{3-6}$cycloalkyl-$C_{1-6}$alkyl. In certain embodiments of formula I, $R^1$ is: $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl. In certain embodiments of formula I, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; tetrahydrofuranyl; tetrahydrofuranyl-$C_{1-6}$alkyl; oxetanyl; or oxetan-$C_{1-6}$alkyl. In certain embodiments of formula I, $R^1$ is: $C_{1-6}$alkyl; halo-$C_{1-6}$alkyl; $C_{1-6}$alkoxy-$C_{1-6}$alkyl; amino-$C_{1-6}$alkyl; or $C_{1-6}$alkylsulfonyl-$C_{1-6}$alkyl. In certain embodiments of formula I, $R^1$ is $C_{1-6}$alkyl. In certain embodiments of formula I, $R^1$ is halo-$C_{1-6}$alkyl. In certain embodiments of formula I, $R^1$ is $C_{1-6}$alkoxy-$C_{1-6}$alkyl. In certain embodiments of formula I, $R^1$ is amino-$C_{1-6}$alkyl. In certain embodiments of formula I, $R^1$ is $C_{1-6}$alkylsulfonyl-$C_{1-6}$alkyl optionally substituted with $C_{1-6}$alkyl. In certain embodiments of formula I, $R^1$ is $C_{3-6}$cycloalkyl optionally substituted with $C_{1-6}$alkyl. In certain embodiments of formula I, $R^1$ is $C_{3-6}$cycloalkyl-$C_{1-6}$alkyl wherein the $C_{3-6}$cycloalkyl portion is optionally substituted with $C_{1-6}$alkyl. In certain embodiments of formula I, $R^1$ is tetrahydrofuranyl. In certain embodiments of formula I, $R^1$ is tetrahydrofuranyl-$C_{1-6}$alkyl; oxetanyl. In certain embodiments of formula I, $R^1$ is or oxetan-$C_{1-6}$alkyl. In certain embodiments of formula I, $R^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl. In certain embodiments of formula I, $R^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl. In certain embodiments of formula I, $R^1$ is: methyl; ethyl; n-propyl; isopropyl; isobutyl; 3,3-dimethylpropyl; cyclopentyl; cyclohexyl; cyclopentylmethyl; methoxyethyl; oxetanyl; or tetrahydrofuranylmethyl. In certain embodiments of formula I, $R^1$ is: methyl; ethyl; n-propyl; isopropyl; or isobutyl. In certain embodiments of formula I, $R^1$ is methyl or ethyl. In certain embodiments of formula I, $R^1$ is methyl. In certain embodiments of formula I, $R^1$ is ethyl. In certain embodiments of formula I, $R^1$ is: cyclopropyl; cyclobutyl; cyclopentyl; cyclohexyl; cyclopropylmethyl; cyclobutylmethyl; cyclopentylmethyl; or cyclopropylethyl. In certain embodiments of formula I, $R^1$ is: cyclopentyl; cyclohexyl; or cyclopentylmethyl.

In certain embodiments of formula I, $R^2$ is: halo; $C_{1-6}$alkoxy; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl. In certain embodiments of formula I, $R^2$ is: halo; $C_{1-6}$alkoxy; halo-$C_{1-6}$alkyl; cyano; $C_{1-6}$alkynyl; $C_{1-6}$alkenyl; $C_{3-6}$cycloalkyl; or $C_{3-6}$cycloalkyl-$C_{1-6}$alkyl. In certain embodiments of formula I, $R^2$ is: halo; $C_{1-6}$alkoxy; halo-$C_{1-6}$alkyl; cyano; $C_{3-6}$cycloalkyl; or $C_{3-6}$cycloalkyl-$C_{1-6}$alkyl. In certain embodiments of formula I, $R^2$ is: halo; $C_{1-6}$alkoxy; halo-$C_{1-6}$alkyl; $C_{3-6}$cycloalkyl; or $C_{3-6}$cycloalkyl-$C_{1-6}$alkyl. In certain embodiments of formula I, $R^2$ is: halo; halo-$C_{1-6}$alkyl; or cyano. In certain embodiments of formula I, $R^2$ is: halo; or halo-$C_{1-6}$alkyl. In certain embodiments of formula I, $R^2$ is halo. In certain embodiments of formula I, $R^2$ is $C_{1-6}$alkoxy. In certain embodiments of formula I, $R^2$ is halo-$C_{1-6}$alkoxy. In certain embodiments of formula I, $R^2$ is halo-$C_{1-6}$alkyl. In certain embodiments of formula I, $R^2$ is $C_{3-6}$cycloalkyl. In certain embodiments of formula I, $R^2$ is $C_{3-6}$cycloalkyl-$C_{1-6}$alkyl. In certain embodiments of formula I, $R^2$ is tetrahydrofuranyl. In certain embodiments of formula I, $R^2$ is tetrahydrofuranyl-$C_{1-6}$alkyl. In certain embodiments of formula I, $R^2$ is oxetanyl. In certain embodiments of formula I, $R^2$ is oxetan-$C_{1-6}$alkyl. In certain embodiments of formula I, $R^2$ is halo, trifluoromethyl or cyano. In certain embodiments of formula I, $R^2$ is chloro, trifluoromethyl or cyano. In certain embodiments of formula I, $R^2$ is chloro or trifluoromethyl. In certain embodiments of formula I, $R^2$ is fluoro, chloro or bromo. In certain embodiments of formula I, $R^2$ is chloro. In certain embodiments of formula I, $R^2$ is fluoro. In certain embodiments of formula I, $R^2$ is bromo. In certain embodiments of formula I, $R^2$ is trifluoromethyl. In certain embodiments of formula I, $R^2$ is methoxy. In certain embodiments of formula I, $R^2$ is cyano. In certain embodiments of formula I, $R^2$ is $C_{1-6}$alkynyl. In certain embodiments of formula I, $R^2$ is $C_{1-6}$alkenyl.

In certain embodiments of formula I, $R^3$ is: $C_{1-6}$alkyl; In certain embodiments of formula I, $R^3$ is halo. In certain embodiments of formula I, $R^3$ is $C_{1-6}$alkyl. In certain embodiments of formula I, $R^3$ is $C_{1-6}$alkoxy. In certain embodiments of formula I, $R^3$ is halo or $C_{1-6}$alkoxy. In certain embodiments of formula I, $R^3$ is $C_{3-6}$cycloalkyloxy. In certain embodiments of formula I, $R^3$ is halo-$C_{1-6}$alkyl. In certain embodiments of formula I, $R^3$ is halo-$C_{1-6}$alkoxy. In certain embodiments of formula I, $R^3$ is halo or methoxy. In certain embodiments of formula I, $R^3$ is fluoro, chloro or methoxy. In certain embodiments of formula I, $R^3$ is fluoro or chloro. In certain embodiments of formula I, $R^3$ is methoxy. In certain embodiments of formula I, $R^3$ is methyl In certain embodiments of formula I, $R^3$ is chloro. In certain embodiments of formula I, $R^3$ is fluoro.

In certain embodiments of formula I, $R^4$ is: $C_{1-6}$alkyl; In certain embodiments of formula I, $R^4$ is halo. In certain embodiments of formula I, $R^4$ is $C_{1-6}$alkyl. In certain embodiments of formula I, $R^4$ is $C_{1-6}$alkoxy. In certain embodiments of formula I, $R^4$ is halo-$C_{1-6}$alkyl. In certain embodiments of formula I, $R^4$ is halo-$C_{1-6}$alkoxy. In certain embodiments of formula I, $R^4$ is halo or methoxy. In certain embodiments of formula I, $R^4$ is $R^4$ is fluoro, chloro, methyl or methoxy. In certain embodiments of formula I, $R^4$ is fluoro, chloro or methoxy. In certain embodiments of formula I, R⁴ is fluoro or chloro. In certain embodiments of formula I, R⁴ is methoxy. In certain embodiments of formula I, R⁴ is methyl In certain embodiments of formula I, R⁴ is chloro. In certain embodiments of formula I, R⁴ is fluoro. In certain embodiments of formula I, R⁴ is C$_{3-6}$cycloalkyloxy.

In certain embodiments of formula I, R³ and R⁴ together with the atoms to which they are attached form a five- or six-membered ring that optionally includes one or two heteroatoms each independently selected from O, N and S, the ring being optionally substituted one or more times with R⁶. In certain embodiments of formula I, R³ and R⁴ together with the atoms to which they are attached form a six-membered ring that includes two oxygen atoms separated by an ethylene group (i.e., R³ and R⁴ together form an ethylene-dioxy group). In certain embodiments of formula I, R³ and R⁴ together with the atoms to which they are attached form a five-membered ring that includes two oxygen atoms separated by a methylene group (i.e., R³ and R⁴ together form a methylene-dioxy group).

In certain embodiments of formula I, R⁵ is C$_{1-6}$alkyl-sulfonyl. In certain embodiments of formula I, R⁵ is C$_{1-6}$alkyl-sulfonyl or cyano. In certain embodiments of formula I, R⁵ is C$_{3-6}$cycloalkyl-sulfonyl. In certain embodiments of formula I, R⁵ is cyano. In certain embodiments of formula I, R⁵ is cyano-C$_{1-6}$alkyl. In certain embodiments of formula I, R⁵ is heterocyclyl optionally substituted with R⁶. In certain embodiments of formula I, R⁵ is heterocyclyl-C$_{1-6}$alkyl wherein the heterocyclyl moiety is optionally substituted with R⁶. In certain embodiments of formula I, R⁵ is halo-C$_{1-6}$alkyl. In certain embodiments of formula I, R⁵ is carboxy. In certain embodiments of formula I, R⁵ is methanesulfonyl. In certain embodiments of formula I, R⁵ is morpholin-4-yl-methyl. In certain embodiments of formula I, R⁵ is morpholinyl. In certain embodiments of formula I, R⁵ is morpholin-4-yl. In certain embodiments of formula I, R⁵ is oxetanyl. In certain embodiments of formula I, R⁵ is oxetan-3-yl. In certain embodiments of formula I, R⁵ is pyrrolidinonyl. In certain embodiments of formula I, R⁵ is pyrrolidin-2-one-1-yl. In certain embodiments of formula I, R⁵ is motpholinonyl. In certain embodiments of formula I, R⁵ is morpholin-3-one-4-yl. In certain embodiments of formula I, R⁵ is piperidinonyl. In certain embodiments of formula I, R⁵ is piperidin-2-one-1-yl. In certain embodiments of formula I, R⁵ is trifluoromethyl In certain embodiments of formula I, R⁵ is heterocycly-sulfonyl wherein the heterocyclyl moiety is optionally substituted one or more times with R⁶. In certain embodiments of formula I, R⁵ is morpholin-4-sulfonyl. In certain embodiments of formula I, R⁵ is morpholin-sulfonyl. In embodiments of the invention wherein R⁵ is heterocyclyl or contains a heterocyclyl moiety, such heterocyclyl may be azepinyl, piperidinyl, piperazinyl, morpholinyl, thiomorpholinyl, tetrahydropyranyl, pyrrolidinyl, tetrahydrofuranyl, azetidinyl or oxetanyl, each optionally substituted one or more times with R⁶. In embodiments of the invention wherein R⁵ is heterocyclyl or contains a heterocyclyl moiety, such heterocyclyl may be piperidinyl, piperazinyl, morpholinyl, thiomorpholinyl, tetrahydropyranyl, tetrahydrofuranyl, oxetanyl, azetidinyl, azepinyl, oxazepinyl, or pyrrolidinyl, each optionally substituted one or more times with R⁶. In embodiments of the invention wherein R⁵ is heterocyclyl or contains a heterocyclyl moiety, such heterocyclyl may be piperidinyl, piperazinyl, morpholinyl, thiomorpholinyl, or pyrrolidinyl, each optionally substituted one or more times with R⁶. In certain embodiments of formula I, R⁵ is: methanesulfonyl; cyano; morpholin-4-yl-methyl; morpholin-4-yl; morpholin-4-yl-sulfonyl; or trifluoromethyl. In certain embodiments of formula I, R⁵ is: methanesulfonyl; cyano; or morpholin-4-yl-methyl. In certain embodiments of formula I, R⁵ is: methanesulfonyl; or cyano. In certain embodiments of formula I, R⁵ is: a carbonyl heterocyclyl where the carbonyl connects the phenyl and heterocyyl is piperidinyl, piperazinyl, morpholinyl, thiomorpholinyl, or pyrrolidinyl.

In certain embodiments, an LRRK2 inhibitor of interest is a compound selected from Compounds 1-8:

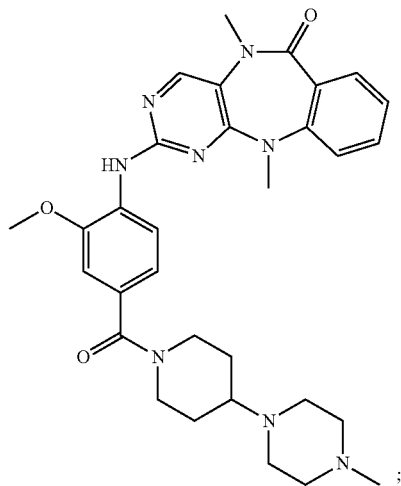

Compound 1

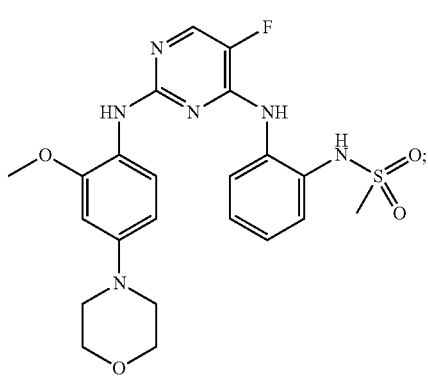

Compound 2

-continued

Compound 3

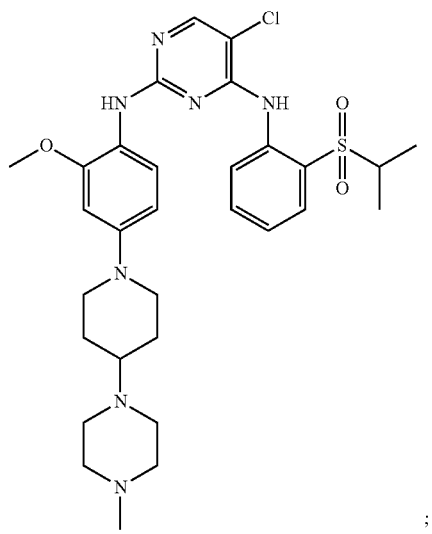

Compound 4

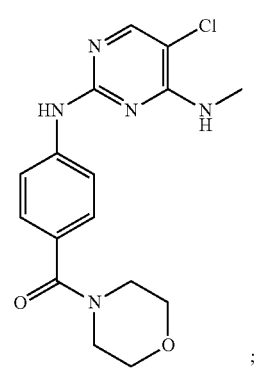

Compound 5

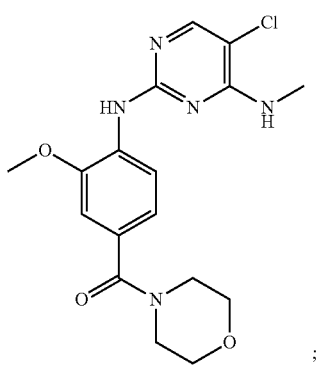

Compound 6

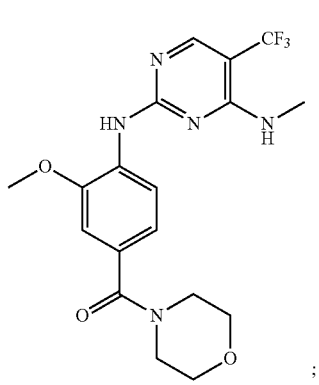

Compound 7

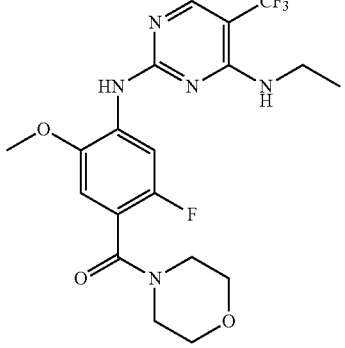

and

Compound 8

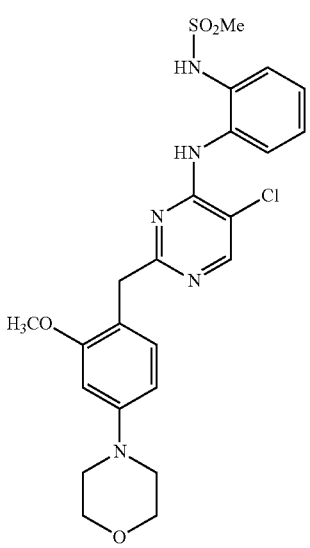

LRRK2 inhibitors that are suitable for use in a subject treatment method include, but are not limited to, a compound of the Formula (Ia):

Formula (Ia)

wherein:
m is from 0 to 3;
X is: —NR$^a$—; —O—; or —S(O)$_r$— wherein r is from 0 to 2 and R$^a$ is hydrogen or C$_{1-6}$alkyl;
R$^1$ is: C$_{1-6}$alkyl; C$_{1-6}$alkenyl; C$_{1-6}$ alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$ alkyl; tetrahydrofuranyl; tetrahydrofuranyl-C$_{1-6}$ alkyl; oxetanyl; or oxetan-C$_{1-6}$ alkyl;
or R$^1$ and R$^a$ together with the atoms to which they are attached may form a three to six membered ring that may optionally include an additional heteroatom selected from O, N and S, and which is substituted with oxo, halo or C$_{1-6}$alkyl;

$R^2$ is: halo; $C_{1-6}$alkoxy; cyano; $C_{1-6}$alkynyl; $C_{1-6}$alkenyl; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$ alkyl;

or $R^1$ and $R^2$ together with the atoms to which they are attached may form a three to six membered ring that may optionally include an additional heteroatom selected from O, N and S, and which is substituted with oxo, halo or $C_{1-6}$alkyl;

Y is a five-membered or six-membered substituted or unsubstituted heterocyclic group, such as substituted or unsubstituted pyrrole, pyrrolidine, pyrazole, pyrazolidine, imidazole, imidazoline, imidazolidine, pyridine, piperidine, pyrazine, piperazine, pyrimidine, indole, purine, benzimidazole, morpholine or quinolone. In some embodiments, Y is a substituted pyrazole.

In certain instances, the LRRK2 inhibitor of Formula Ia is Compound 9.

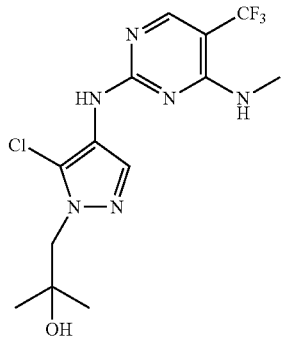

Compound 9

In some embodiments, LRRK2 inhibitors of interest include a compound of Formula (II):

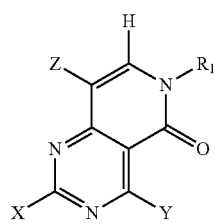

Formula (II)

wherein in one embodiment, $R^1$ is H and X is $NR^2R^3$ or $NR^4R^5$; and Y is $NHR^6$ and Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano, such that:

$R^2$ and $R^3$, taken together with the nitrogen atom to which they are bonded form: i) a 3-8 membered saturated or partially saturated monocyclic group having no heteroatom other than the nitrogen atom to which $R^2$ and $R^3$ are bonded, wherein said 3-8 membered saturated or partially saturated monocyclic group is independently substituted at one or more carbon atoms with 1-2 $R^7$ and optionally substituted at one or more carbon atoms with 0-4 $R^8$, wherein $R^7$ is hydroxy, heterocycloalkyl, or $NR^9R^9$ and $R^8$ is hydroxy($C_1$-$C_6$)alkyl, aryl, $COOR^S$, $(CH_2)_nNR^9R^9$, or $(CH_2)_nNR^9R^{10}$, wherein each n is independently 1, 2, or 3 and the aryl is optionally substituted with halo; or ii) an 8-10 membered bicyclic aryl group having 0-5 heteroatoms independently selected from nitrogen, oxygen, sulfur, sulfoxide, or sulfone;

each $R^9$ is independently selected from H, $C_1$-$C_6$ alkyl, $C_3$-$C_6$ alkynyl, $C_2$-$C_6$ alkyl cyano, $C_2$-$C_6$ alkyl sulfone, $C_3$-$C_6$ cycloalkyl sulfone, $C_2$-$C_6$ sulfonamide, $C_3$-$C_6$ cycloalkyl, $C_3$-$C_8$ heterocycloalkyl, aryl, aryl($C_1$-$C_6$)alkyl, or heteroaryl, wherein the alkyl, alkynyl, alkylcyano, alkylsulfone, sulfonamide, cycloalkyl, heterocycloalkyl, aryl, arylalkyl, or heteroaryl is optionally substituted with $R^{25}$;

$R^{10}$ is $C(O)R^9$, $COOR^9$, $C(O)NR^9R^9$, or $S(O)_nR^9$, in which n is 1 or 2;

$R^4$ is selected from H, $C_1$-$C_6$ alkyl, or hydroxy($C_1$-$C_6$) alkyl; $R^5$ is aryl($C_1$-$C_3$)alkyl, wherein the aryl group is independently substituted at one or more carbon atoms with 1-3 $R^{11}$, wherein $R^{11}$ is independently selected from $OR^9$, $NR^9R^9$, $NR^9COR^9$, or $NR^9S(O)_nR^9$, wherein n is 1 or 2; $R^6$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, or heteroaryl, in which the heterocycloalkyl, aryl, or heteroaryl heteroaryl of $R^6$ is optionally substituted with an aryl selected from the group consisting of: i) a 5-6 membered monocyclic aryl group; ii) an 8-10 membered bicyclic aryl group having 0-5 heteroatoms independently selected from nitrogen, oxygen, sulfur, sulfoxide, or sulfone; iii) an 8-10 membered unsaturated or partially unsaturated bicyclic aryl group having 0-5 heteroatoms independently selected from nitrogen, oxygen, sulfur, sulfoxide, or sulfone; and iv) an 8-10 membered unsaturated or partially unsaturated bicyclic aryl group having a carbonyl, carboxamide, or sulfoxamide; or the heterocycloalkyl, aryl, or heteroaryl of $R^6$ can be also optionally substituted at one or more carbon atoms with $R^{12}$, wherein each $R^{12}$ is independently selected from $C_1$-$C_6$ alkyl, $CF_3$, $OCF_3$, $S(O)_n$($C_1$-$C_4$)alkyl, halo($C_1$-$C_4$)alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl ($C_1$-$C_6$)alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O)NR^{13}R^{13}$, $CONR^{15}R^{16}$, $S(O)_nR^{13}$, $S(O)_nNR^{13}R^{13}$, or $NR^{15}R^{16}$, wherein each n is independently 1 or 2 and the alkyl, alkenyl, alkynyl, cyclolalkyl, heterocycloalkyl, cycloalkenyl, aryl, arylalkyl, haloalkyl, or heteroaryl is optionally substituted with $R^{25}$, wherein the aryl and heteroaryl of $R^{12}$ is independently selected from: i) a 5-6 membered monocyclic aryl group; ii) an 8-10 membered bicyclic aryl group having 0-5 heteroatoms independently selected from nitrogen, oxygen, sulfur, sulfoxide or sulfone; iii) an 8-10 membered unsaturated or partially unsaturated bicyclic aryl group having 0-5 heteroatoms independently nitrogen, oxygen, sulfur, sulfoxide or sulfone; or iv) an 8-10 membered unsaturated or partially unsaturated bicyclic aryl group having a carbonyl, carboxamide, or sulfoxamide; each $R^{13}$ is independently selected from H, $C_1$-$C_6$ alkyl, $C_2$-$C_6$ alkenyl, $C_3$-$C_6$ alkynyl, $C_2$-$C_6$ alkyl cyano, $C_2$-$C_6$ alkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl or heteroaryl, wherein the alkyl, alkenyl, alkynyl, alkyl cyano, alkyl sulfone, alkyl sulfonamide, cycloalkyl, heterocycloalkyl, cycloalkenyl, aryl, arylalkyl, haloalkyl, or heteroaryl is optionally substituted with $R^{25}$; $R^{14}$ is C(O) $R^{13}$, $COOR^{13}$, $C(O)NR^{13}R^{13}$, $SO_2NR^{13}R^{13}$, or $S(O)_nR^{13}$, wherein n is 1 or 2;

$R^{15}$ and $R^{16}$, taken together with the nitrogen atom to which they are bonded, form: i) a 3-8 membered saturated or partially saturated monocyclic group, wherein the 3-8 membered saturated or partially saturated monocyclic group is optionally substituted with $R^{25}$; ii) an 8-12 membered saturated or partially saturated bicyclic group, wherein the 8-12 membered saturated or partially saturated bicyclic group is optionally substituted with $R^{25}$; iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or iv) a 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$; and each $R^{25}$ is independently selected from hydroxy, hydroxy($C_1$-$C_6$)alkyl, $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl($C_1$-$C_6$)alkyl, aryl, halo, haloalkyl, oxo, oxime, $CF_3$, $SR^{13}$, $OCF_3$, $OR^{13}$, $OC(O)CH_2R^{13}$, $NR^{13}R^{13}$, $NR^{13}R^{14}$, $NHC(O)R^{13}$, $(CH_2)_nNR^{13}R^{13}$, $COOR^{13}$, CN, $C(O)R^{13}$, $C(O)CF_3$, $CONR^{15}R^{16}$, $CONH_2$, $S(O)_6R^{13}$, $S(O)_nNR^{13}R^{13}$, or $NR^{15}R^{16}$, wherein each n is independently 1 or 2 and the heterocycloalkyl is optionally substituted with $C_1$-$C_3$ alkyl.

In some embodiments, LRRK2 inhibitors of interest include a compound of Formula (II):

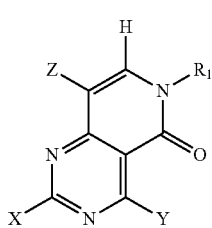

Formula (II)

wherein in one embodiment, $R^1$ is $CH_3$ and X is X is $NH_2$ or $NHR^6$; and Y is $NHR^6$ or $R^6$ and Z is H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl, or heteroaryl is optionally substituted with halo, alkyl, or cyano.

In some embodiments, $R^1$ is H, X is $NR^4R^5$, and Y is $NHR^6$. Z can be H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl, or heteroaryl is optionally substituted with halo, alkyl, or cyano such that $R^4$ is selected from H, $C_1$-$C_6$ alkyl, or hydroxy($C_1$-$C_6$)alkyl and $R^5$ is aryl($C_1$-$C_3$)alkyl. The aryl group of aryl($C_1$-$C_3$)alkyl of $R^5$ is independently substituted at the one or more carbon atoms with 1-3 $R^{11}$. $R^{11}$ is independently selected from $OR^9$, $NR^9R^9$, $NR^9COR^9$, or $NR^9S(O)_nR^9$, in which n is 1 or 2. $R^9$ is independently selected from H, $C_1$-$C_6$ alkyl, $C_2$-$C_6$ alkenyl, $C_3$-$C_6$ alkynyl, $C_2$-$C_6$ alkyl cyano, $C_2$-$C_6$ alkyl sulfone, $C_3$-$C_6$ alkyl sulfone, $C_3$-$C_6$ cycloalkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl, or heteroaryl, in which the alkyl, alkenyl, alkynyl, alkyl cyano, alkyl sulfone, sulfonamide, cycloalkyl, heterocycloalkyl, cycloalkenyl, aryl, arylalkyl, haloalkyl, or heteroaryl is optionally substituted with $R^{25}$.

In some instances, Y is $NHR^6$ and $R^6$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$.

In some embodiments, LRRK2 inhibitors of interest include a compound of Formula (III):

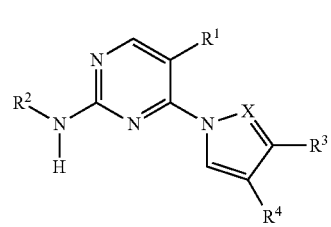

Formula (III)

wherein: X is CH or N;

$R^1$ is selected from H, halo, CN, $C_1$-$C_{10}$ alkyl or halo($C_1$-$C_4$)alkyl, wherein $C_1$-$C_{10}$ alkyl, or halo($C_1$-$C_4$)alkyl is optionally substituted;

$R^2$ is aryl, cycloalkyl, arylalkyl, or heterocyclyl, wherein the aryl, cycloalkyl, arylalkyl, or heterocyclyl is optionally and independently substituted at one or more carbon atoms with 1-4 $R^5$ or $R^{5a}$ groups; and wherein aryl and heterocyclyl having one or more nitrogen atoms is optionally and independently substituted at one or more nitrogen atoms with 1-4 $R^6$ or $R^{6a}$ groups;

$R^3$ is independently halo, CN, or $R^7$; and $R^4$ is selected from $(CH_2)_nOH$, $(CH_2)_nNR^{11}R^{12}$, $C(O)NHR^7$, $C(O)NR^{11}R^{12}$, $C(O)R^7$, $C(O)NR^7R^7$, $C(O)NR^7R^8$, $(CH_2)_nNR^7R^7$, $(CH_2)_nNR^7R^8$, $(CH_2)_nCN$, $(CH_2)_nSR^7$, $(CH_2)_nS(O)_nR^7$, or $(CH_2)_nS(O)_nNR^7R^7$, wherein each n is independently 1 or 2; wherein:

Each $R^5$ is independently selected from halo, $CF_3$, $SR^7$, $OR^7$, $OC(O)R^7$, $O(CH_2)_nNR^7R^7$, $O(CH_2)_nNR^{11}R^{12}$, $O(CH_2)_nR^7$, $O(CH_2)_nC(O)NR^{11}R^{12}$, $O(CH_2)_nC(O)NR^7R^7$, $NR^7R^7$, $NR^7R^8$, $NHC(O)NH_2$, $C(O)OR^7$, $NO_2$, CN, $C(O)R^7$, $OSO_2CH_3$, $S(O)_nR^7$, $S(O)_nNR^7R^7$, $NR^7C(O)NR^7R^7$, $NR^7C(O)R^7$, $NR^7C(O)OR^7$, $NR^7S(O)_nR^7$, or $NR^{11}R^{12}$, wherein each n is independently 1 or 2;

Each $R^{5a}$ is independently selected from amino, halo, hydroxy, $C_1$-$C_{10}$ alkyl, $C_2$-$C_{10}$alkenyl, $C_3$-$C_{10}$ alkynyl, $C_3$-$C_{12}$cycloalkyl, $C_5$-$C_{10}$cycloalkenyl, alkoxy, haloalkyl, aryl, heteroaryl, or heterocyclyl, wherein the $C_1$-$C_{10}$ alkyl, $C_2$-$C_{10}$alkenyl, $C_3$-$C_{10}$alkynyl, $C_3$-$C_{12}$cycloalkyl, $C_5$-$C_{10}$cycloalkenyl, alkoxy, haloalkyl, aryl, heteroaryl, or heterocyclyl is optionally and independently substituted with 1 to 3 groups selected from halo, hydroxy, alkyl, $R^9$, or $R^{10}$; Each $R^6$ is independently $R^7$, $C(O)CH_2CN$, $C(O)R^7$, $C(O)OR^7$, $CO_2(C_1$-$C_6$alkyl), $C(O)NR^7R^7$, $SO_2NR^7R^7$, or $SO_2R^7$;

Each $R^{6a}$ is independently hydroxy, $C_1$-$C_{10}$ alkyl, $C_2$-$C_{10}$ alkenyl, $C_3$-$C_{10}$ alkynyl, $C_3$-$C_{12}$ cycloalkyl, $C_5$-$C_{10}$ cycloalkenyl, haloalkyl, wherein each $R^{6a}$ group is optionally and independently substituted with 1-3 groups selected from hydroxy, aryl, alkyl, halo, $R^9$, or $R^{10}$;

Each $R^7$ is independently H, $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl, wherein the $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl is optionally and independently substituted with 1-4 groups selected from aryl, cycloalkyl, heteroaryl, heterocyclyl, alkyl, halo, amino, hydroxy, $R^9$, or $R^{10}$;

Each $R^8$ is independently $C(O)R^7$, $C(O)OR^7$, $C(O)NR^7R^7$, or $S(O)_nR^7$, wherein n is 1 or 2; Each $R^9$ is independently $CF_3$, $SR^7$, $OR^7$, $NR^7R^7$, $NR^{11}R^{12}$, $C(O)NR^7R^7$, $C(O)NR^{11}R^{12}$, $S(O)_nNR^7R^7$, or $S(O)_nR^7$, wherein each n is independently 1 or 2;

Each $R^{10}$ is $C(O)O(C_1-C_6)$alkyl, or halo$(C_1-C_4)$alkyl; and $R^{11}$ and $R^{12}$, taken together with the nitrogen atom to which they are bonded form: i) a 3-8 membered saturated or partially saturated ring having no heteroatom other than the nitrogen atom to which $R^{11}$ and $R^{12}$ are bonded, wherein said 3-8 membered saturated or partially saturated ring is optionally and independently substituted with 1-4 groups selected from $R^5$ or $R^{5a}$ at one or more substitutable carbon atoms; ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$; iii) a 9-10 membered saturated or partially saturated bicyclic ring having no heteroatom other than the nitrogen atom to which $R^{11}$ and $R^{12}$ are bonded, wherein said 9-10 membered saturated or partially saturated bicyclic ring having no heteroatom is optionally substituted with 1-4 groups independently selected from $R^5$ or $R^{5a}$ at one or more substitutable carbon atoms; iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide; or v) a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$; or a pharmaceutically acceptable salt thereof.

In some embodiments, LRRK2 inhibitors of interest include a compound of the Formula (IV):

Formula (IV)

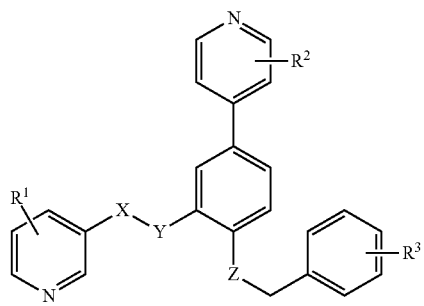

wherein:
m is from 0 to 3;
X is: —$NR^a$; —O—; or —$S(O)_r$— wherein r is from 0 to 2 and $R^a$ is hydrogen or $C_{1-6}$alkyl;
Y is a bond; oxo; —O—; or —$S(O)_r$— wherein r is from 0 to 2.
Z is a bond; oxo; —$NR^a$; —O—; or —$S(O)_r$— wherein r is from 0 to 2 and $R^a$ is hydrogen or $C_{1-6}$alkyl;
$R^1$, $R^2$ and $R^3$ are each independently hydrogen, $C_{1-6}$alkyl; $C_{1-6}$alkenyl; $C_{1-6}$ alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$ alkyl; tetrahydrofuranyl; tetrahydrofuranyl-$C_{1-6}$ alkyl; oxetanyl; or oxetan-$C_{1-6}$ alkyl;

In certain instances, the LRRK2 inhibitor of Formula IV is Compound 10.

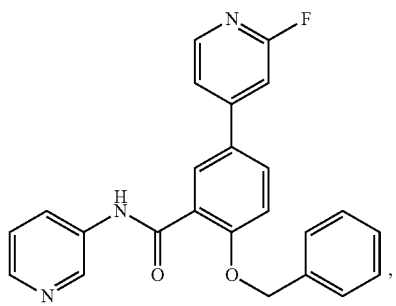

Compound 10

In some embodiments, LRRK2 inhibitors of interest include a compound of Formula (IVa):

Formula (IVa)

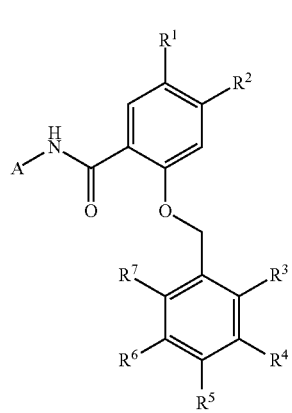

wherein A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

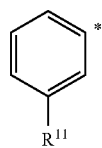

wherein when A represents pyridin-3-yl, the pyridinyl ring may optionally be substituted at the 2 position by fluoro, methoxy or CH$_2$OH, at the 4 position by methyl or CH$_2$OH, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl:

R$^1$ and R$^2$ independently represent halo, C$_{1-3}$ haloalkyl, —(CH$_2$)$_n$R$^8$, —(CO)R$^8$, nitrogen containing heteroaryl ring optionally substituted with one two or three groups selected from methyl and trifluoromethyl;

n represents 1, 2 or 3;

R$^3$, R$^4$, R$^5$, R$^6$ and R$^7$ independently represent hydrogen, halo, CN, C$_{1-3}$alkyl or C$_{1-3}$alkoxy;

R$^8$ represents hydrogen or —NR$^9$R$^{10}$, R$^9$ and R$^{10}$ are either independently selected from hydrogen and C$_{1-3}$ alkyl, wherein said C$_{1-3}$ alkyl group is optionally substituted with one two or three halo, hydroxy, cyano or C$_{1-2}$alkoxy groups, or together with the nitrogen atom to which they are attached, join together to form a nitrogen containing mono-heterocyclic ring which ring is optionally substituted with one, two or three groups selected from halo, methyl and trifluoromethyl; and R$^{11}$ represents hydrogen, halo, CN, —CH$_{1-2}$alkyl, C$_{1-2}$alkoxy, —CH$_2$CO$_2$H or —CONHCH$_3$.

In some embodiments, LRRK2 inhibitors of interest include a compound of Formula (V):

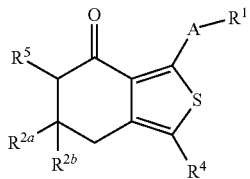

Formula (V)

where A is —CH$_2$— and —R$^1$ is —C$_{1-10}$-alkyl; or A is: —S—; —SO—; —SO$_2$—; —O—; or —NR$^a$, wherein —R$^a$ is —H, —C$_{1-20}$-alkyl, or —R$^a$ is taken together with —R$^1$ to form a cyclo-amino moiety of the formula:

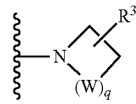

wherein q is an integer of 1 to 4, W is —CH$_2$— or —(N—C$_{1-20}$-alkyl)-, —R$^3$ is one or more moieties which are independently: —OH; —C$_{1-6}$-alkyl; —C$_{1-6}$-alkoxy, and wherein, when A is not (—CH$_2$—), —R$^1$ is:

(a) —C$_{1-8}$-alkyl, optionally substituted independently for each occurrence with: (i) —(N=N$^+$=N$^-$); (ii) -halogen; (iii) —C$_{1-8}$-alkoxy, optionally substituted; (iv) —OH; (v) morpholinyl-; (vi) pyridyl-; (vii) moieties of the formula (—N(R$^b$)$_2$), where —R$^b$ is independently —H or —C$_{1-10}$-alkyl; (viii) furanyl-; (ix) -aryl, optionally substituted, independently for each occurrence, with: (1) —NR$^c$—(C=O)—CH$_3$, where —R$^c$ is —H or —C$_{1-6}$-alkyl; (2) -alkoxy; (3) halogen-; (x) -aryloxy; (xi) a moiety of formula:

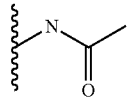

or formula:

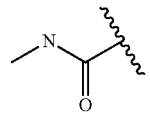 [SMILES: *C(=O)NC]

or a moiety of formula

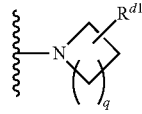

wherein, "q" is an integer of 1 to 4, and wherein independently, for each occurrence, a ring carbon is optionally substituted with —R$^{d1}$, wherein —R$^{d1}$ is —C$_{1-6}$-alkyl; (xiii) a moiety of the formula —CH=CHR$^{d2}$, wherein —R$^{d2}$ is —H or —C$_{1-6}$-alkyl; (xiv) —Si(R$^e$)$_3$, wherein —R$^e$ is a —C$_{1-4}$-alkyl which is optionally substituted with -fluorine;

(b) thiopenyl-;
(c) heteroaryl-;
(d) pyridyl-;
(e) furanyl-;
(f) -aryl, optionally substituted, independently for each occurrence with: (i) —N(R$^f$)—(C=O)—CH$_3$, wherein —R$^f$ is —H or —C$_{1-6}$-alkyl; (ii) —C$_{1-20}$-alkoxy; or (iii) halogen-;
(g) a moiety of the formula:

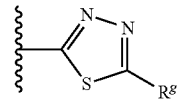

wherein —R$^g$ is —C$_{1-6}$-alkyl or —S—C$_{1-6}$-alkyl; —R$^{2a}$ and a R$^{2b}$ are independently —C$_{1-6}$-alkyl or —H; —R$^4$ is a substituent of the formula:

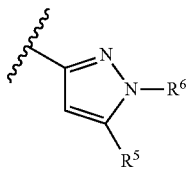

wherein: —R$^6$ is: (a) —H; (b) —C$_{1-6}$-alkyl; (c) —SO$_2$—C$_{1-6}$-alkyl; (d) —(C=O)—NH—R$^h$, wherein —R$^h$ is: (I) —(CH$_2$)$_{0-4}$—C$_{6-10}$-aryl, the -aryl moiety optionally comprising up to three substituents which are independently for each occurrence: (i) -halogen; (ii) —O—C$_{1-6}$-alkyl; (iii) —S—C$_{1-6}$-alkyl or (iv) —CN; (II) pyridinyl-, optionally substituted, independently for each occurrence, with -halogen; (III) piperidinyl-, which is bonded to the substrate through a carbon atom of the ring, and is optionally N-substituted with an acyl-moiety; or (IV) —$C_{1-8}$-alkyl; (e) —(C═O)—$CH_2$—$R^i$, wherein —$R^i$ is: (i) —H; (ii) p-chlorobenzyl-; (iii) —$C_{1-6}$-alkyl; or (iv) —$C_{1-20}$-alkoxy; or (f) —(C═O)—$R^k$, wherein —$R^k$ is: (i) —$C_{1-6}$-alkyl; (ii) phenyl-, optionally substituted with up to 3 substituents which are independently for each occurrence: cyano-; halogen-; or —$C_{1-6}$-alkoxy (—O—$C_{1-6}$-alkyl); or (iii) —(NH)—$C_{1-6}$-linear-alkyl-aryl; and —$R^5$ is: (a) —H; (h) —$C_{1-6}$-alkyl; or (c)-$(CH_2)_{0-4}$—$C_{6-10}$-aryl, wherein the -aryl moiety is optionally substituted by up to three substituents which are independently for each occurrence: (i) -halogen; (ii) —O—$C_{1-6}$-alkyl; (iii) —S—$C_{1-6}$-alkyl or (iv) —CN.

In some embodiments, LRRK2 inhibitors of interest include a compound of Formula (VI):

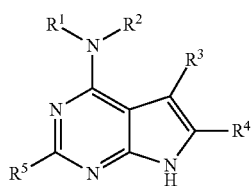

Formula (VI)

or a pharmaceutically acceptable salt thereof wherein:

$R^1$ and $R^2$ are each independently hydrogen, $C_1$-$C_6$alkyl, $C_3$-$C_7$cycloalkyl, a four to seven membered heterocycloalkyl which contains one to three heteroatoms selected from N, O and S; or a five to six membered heteroaryl which contains one to four heteroatoms selected from N, O and S, wherein the $C_1$-$C_6$alkyl, $C_3$-$C_7$cycloalkyl, four to seven membered heterocycloalkyl, or five to six membered heteroaryl are optionally substituted with one to three $R^6$; or $R^1$ and $R^2$ taken together with the nitrogen to which they are attached are a four to seven membered heterocycloalkyl which optionally contains one to two additional heteroatoms selected from N, O and S, and optionally contains one double bond; a six to eleven membered heterobicycloalkyl which optionally contains one to two additional heteroatoms selected from N, O and S; or a six to twelve membered heterospirocycloalkyl which optionally contains one to two additional heteroatoms selected from N, O and S; and wherein the four to seven membered heterocycloalkyl, six to eleven membered heterobicycloalkyl or six to twelve membered heterospirocycloalkyl is optionally substituted with one to three $R^7$;

$R^3$ is phenyl or a five to ten membered heteroaryl which contains one to four heteroatoms selected from N, O and S; wherein the phenyl and five to ten membered heteroaryl are optionally substituted with one to three $R^9$ and wherein the phenyl is optionally fused with a $C_5$-$C_6$cycloalkyl or a five to six membered heterocycloalkyl which contains one to three heteroatoms selected from N, O and S and which is optionally substituted with oxo;

$R^4$ and $R^5$ are each independently hydrogen or $C_1$-$C_3$alkyl;

$R^6$ at each occurrence is independently selected from $C_1$-$C_3$alkyl, $C_1$-$C_3$alkoxy, hydroxy, halo, —$NR^aR^b$, —C(O)$NR^aR^b$, or a four to seven membered heterocycloalkyl which contains one to three heteroatoms selected from N, O and S;

$R^7$ at each occurrence is independently selected from halo, hydroxy, cyano, $NR^aR^b$, —C(O)$NR^aR^b$, $C_1$-$C_6$alkyl, $C_1$-$C_6$alkoxy, phenyl, a five to six membered heteroaryl containing one to four heteroatoms selected from N, O and S, or two $R^7$ when attached to the same carbon and taken together can be oxo; wherein the $C_1$-$C_6$alkyl, phenyl and five to six membered heteroaryl are optionally substituted with one to three $R^8$;

$R^8$ at each occurrence is independently hydroxy, halo, cyano, $C_1$-$C_3$alkoxy, $NR^aR^b$, $C_1$-$C_3$alkyl optionally substituted with one to three halo, $C_3$-$C_7$cycloalkyl, phenoxy optionally substituted with cyano, or a five to six membered heteroaryloxy containing one to four heteroatoms selected from N, O and S and which is optionally substituted with one or two halo or $C_1$-$C_3$alkyl;

$R^9$ at each occurrence is independently cyano, halo, hydroxy, $C_1$-$C_3$alkyl-S—, —$CO_2H$, —C(O)$NH_2$, —S(O)$_2$$NH_2$, $C_1$-$C_3$alkyl optionally substituted with one to three halo or hydroxy, or $C_1$-$C_3$alkoxy optionally substituted with one to three halo or hydroxy; and $R^a$ and $R^b$ at each occurrence are each independently hydrogen, $C_1$-$C_6$alkyl, $C_3$-$C_7$cycloalkyl or —C(O)$C_1$-$C_6$alkyl.

In certain embodiments, LRKK2 inhibitors of interest include a 2,4-diaminopyrimidine compound as described in Chen et al. ("Discovery of Selective LRRK2 Inhibitors Guided by Computational Analysis and Molecular Modeling"; *J. Med. Chem.* 55:5536), aminopyrimidines as described in Kramer et al. ("Small Molecule Kinase Inhibitors for LRRK2 and Their Application to Parkinson's Disease Models"; *ACS Chem. Neurosci.* 3:151); LRRK2 inhibitors described in Lee et al. ("Inhibitors of leucine-rich repeat kinase-2 protect against models of Parkinson's disease" *Nat. Med.* 16:998); aminopyrimidines as described in Deng et al. ("Characterization of a selective inhibitor of the Parkinson's disease kinase LRRK2" *Nat. Chem. Biol.* 7:203), the disclosures of which are herein incorporated by reference.

Also included are pharmaceutically acceptable salts, tautomers, geometric isomers, enantiomers, diasterioisomers, and racemates of a compound of one of Formulas I-VI.

In still other embodiments, suitable LRRK2 inhibitors include LRRK2 inhibitors as described in International Patent Applications WO2014/060113, WO2014/0601112, WO2012/143144, WO2013/079494, WO2013/079505, WO2013/046029, WO2012/058193, WO2012/178015, as well as LRRK2 inhibitors as described in United States Patent Publication Nos. US20140005183; US20130338106; US20130225584; US2013158032; US20130157999; US20130296317; US20120329785; US20120329780, and U.S. Pat. Nos. 8,629,132 and 8,404,677, the disclosures of which are herein incorporated by reference.

In some cases, a suitable LRRK2 inhibitor has a half maximal inhibitory concentration ($IC_{50}$) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

Whether a given compound inhibits LRRK2 enzymatic activity can be determined using any known method, including, e.g., a method as described in U.S. Patent Publication No. 2013/0158032, or in Taymans et al. (2011) *PLoSOne* 6:e23207; or in Vancraenenbroeck et al. (2014) *Front. Mol. Neurosci.* 7:51.

The following is an example of a suitable assay. LRRK2 is contacted in a reaction mixture with: γ-$^{32}$P-ATP, LRRK2 peptide substrate (RLGRDKYKTLRQIRQ; SEQ ID NO://), 10 μM ATP, and kinase buffer; and: 1) a test compound (e.g., a putative LRRK2 inhibitor); 2) a negative control; or 3) a positive control. Kinase buffer can be 25 mM Tris, pH 7.5; 10 mM MgCl$_2$; 2 mM dithiothreitol; 0.2% Triton (non-ionic detergent); 5 mM β-glycerophosphate; and 0.1 mM Na$_3$VO$_4$. The reaction mixture is kept at 30° C. for 30 minutes. The reaction is stopped by addition of 500 mM EDTA. LRRK peptide substrate phosphorylation levels are measured via autoradiography after spotting the stopped reaction mixtures on phosphocellulose paper.

In some cases, a suitable LRRK2 inhibitor is a selective LRRK2 inhibitor. For example, in some cases, a suitable LRRK2 inhibitor inhibits enzymatic (kinase) activity of LRRK2 but does not substantially inhibit an enzyme (e.g., a kinase) other than LRRK2. For example, in some cases, a suitable LRRK2 inhibitor inhibits enzymatic (kinase) activity of LRRK2 by at least about 50%, at least about 60%, at least about 70%, at least about 80%, at least about 90%, or more than 90%, at a given concentration (e.g., 1 μM or 10 μM), but does not substantially inhibit an enzyme other than LRRK2; for example, the LRRK2 inhibitor inhibits an enzyme other than LRRK2 by less than 25%, less than 15%, less than 10%, or less than 5%, or does not detectably inhibit an enzyme other than LRRK2, at the same concentration of LRRK2.

In some cases, a suitable LRRK2 inhibitor is an agent that inhibits LRRK2 GTPase activity. For example, in some cases, a suitable LRRK2 inhibitor is an agent that inhibits LRRK2 GTPase activity by at least 10%, at least 15%, at least 20%, at least 25%, at least 30%, at least 40%, at least 50%, at least 60%, at least 70%, at least 80%, at least 90%, or more than 90%, compared to the level of GTPase activity in the absence of the agent.

In some cases, an agent that inhibits LRRK2 GTPase is a compound of the following structure:

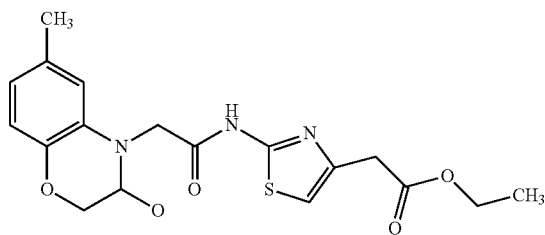 [SMILES: CCOC(=O)Cc1csc(NC(=O)CN2c3cc(C)ccc3OCC2O)n1]

In some cases, an agent that inhibits LRRK2 GTPase is a compound of the following structure:

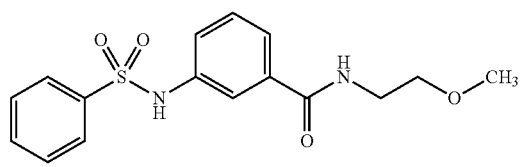 [SMILES: COCCNC(=O)c1cccc(NS(=O)(=O)c2ccccc2)c1]

In some cases, a suitable LRRK2 inhibitor is an agent that reduces ARFGAP1 activation of LRRK2 GTPase activity. For example, in some cases, a suitable LRRK2 inhibitor is an agent that reduces ARFGAP1 activation of LRRK2 GTPase activity by at least 10%, at least 15%, at least 20%, at least 25%, at least 30%, at least 40%, at least 50%, at least 60%, at least 70%, at least 80%, at least 90%, or more than 90%, compared to the level of ARFGAP1 activation of LRRK2 GTPase activity in the absence of the agent. In some cases, an agent that ARFGAP1 activity is QS 11. See, e.g., Zhang et al. (2007) *Proc. Natl. Acad. Sci. USA* 104:7444. The structure of QS 11 is as follows:

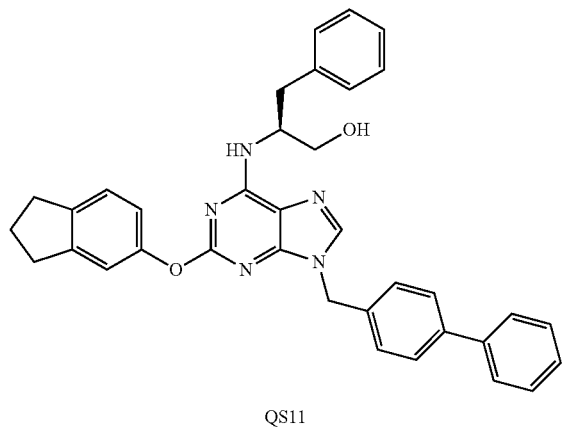 [SMILES: OC[C@H](Cc1ccccc1)Nc1nc(Oc2ccc3c(c2)CCC3)nc2c1ncn2Cc1ccc(-c2ccccc2)cc1]

QS11

Dosages, Formulations, and Routes of Administration

In the subject methods, an active agent (e.g., an LRRK2 inhibitor) and optionally one or more additional antiviral agents) may be administered to the host using any convenient means capable of resulting in the desired therapeutic effect. Thus, the agent can be incorporated into a variety of formulations for therapeutic administration. More particularly, the agents of the embodiments can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. An LRRK2 inhibitor is generally referred to below as an "agent" or an "active agent."

Formulations

The above-discussed active agent(s) can be formulated using well-known reagents and methods. Compositions are provided in formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

As such, administration of the agents can be achieved in various ways, including oral, buccal, rectal, parenteral, intraperitoneal, intradermal, subcutaneous, intramuscular, transdermal, intratracheal, etc., administration. In many embodiments, administration is by bolus injection, e.g., subcutaneous bolus injection, intramuscular bolus injection, and the like.

The pharmaceutical compositions of the embodiments can be administered orally, parenterally or via an implanted reservoir. In some cases, an LRRK2 inhibitor is administered via oral administration. In some cases, an LRRK2 inhibitor is administered by injection, e.g., by intramuscular injection, by subcutaneous injection, or by intravenous injection.

Subcutaneous administration of a pharmaceutical composition of the embodiments is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a pharmaceutical composition of the embodiments to a patient through the port is referred to herein as "a subcutaneous injection port delivery system." In many embodiments, subcutaneous administration is achieved by bolus delivery by needle and syringe.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the unit dosage forms depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

The daily dosage of an LRRK2 inhibitor will vary with the compound employed, the mode of administration, the treatment desired and the disease indicated, as well as other factors such as a subject's age, body weight, general health, condition, prior medical history and sex, and like factors known in the medical arts. For example, in some cases, an LRRK2 inhibitor is administered at a daily dosage in the range from about 0.5 mg/kg body weight to about 15 mg/kg body weight, e.g. in the range from about 1 mg/kg body weight to about 10 mg/kg body weight. As another example, in some cases, an LRRK2 inhibitor is administered at a daily dosage from about 0.001 g to about 1.5 g, e.g., not exceeding about 1 gram, e.g. from about 0.1 g to about 0.5 g for a 70 kg human, given up to 4 times daily.

An LRRK2 inhibitor is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

In many embodiments, multiple doses of an LRRK2 inhibitor are administered. For example, an LRRK2 inhibitor is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). In some cases, an LRRK2 inhibitor is administered substantially continuously, or continuously, over a period of time ranging from about one day to about one week, from about two weeks to about four weeks, from about one month to about two months, from about two months to about four months, from about four months to about six months, or more.

Routes of Administration

An active agent (e.g., an LRRK2 inhibitor) can be administered via a variety of routes of administration, including oral, buccal, rectal, parenteral, intraperitoneal, intravenous, intradermal, subcutaneous, intramuscular, transdermal, intratracheal, etc., administration. In some embodiments, administration is by bolus injection, e.g., subcutaneous bolus injection, intramuscular bolus injection, and the like. In some cases, an LRRK2 inhibitor is administered via oral administration. In some cases, an LRRK2 inhibitor is administered via subcutaneous administration. In some cases, an LRRK2 inhibitor is administered via intravenous administration. In some cases, an LRRK2 inhibitor is administered via intramuscular. In some cases, an LRRK2 inhibitor is administered via inhalation.

Individuals Suitable for Treatment

Individuals who are suitable for treatment with a method of the present disclosure include individuals who have been diagnosed as having a flavivirus (e.g., Dengue virus) infection. Individuals who are suitable for treatment with a method of the present disclosure include individuals who have been diagnosed as having a flavivirus (e.g., Dengue virus) infection; and who exhibit dengue hemorrhagic fever. Individuals who are suitable for treatment with a method of the present disclosure include individuals who have been diagnosed as having a flavivirus (e.g., Dengue virus) infection; and who exhibit dengue shock syndrome (DSS).

Individuals who are suitable for treatment with a method of the present disclosure include individuals who have an acute dengue infection (e.g., have been diagnosed as having an acute dengue infection).

In some cases, individuals having Parkinson's disease are specifically excluded.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Inhibition of Dengue Virus with LRRK2 Inhibitors

Dengue Virus (DENV) Capsid Interacts with LRRK2

293T cells were transfected with the indicated expression construct (5 μg) and incubated for 48 hours. Cells were then lysed in RIPA buffer for 30 minutes and insoluble debris was removed by centrifugation. Equal amounts of protein lysate (1 mg) were incubated with anti-Strep beads (Invitrogen) overnight at 4 degrees Celsius. Bound proteins were denatured and separated by sodium dodecyl sulfate-polyacrylamide gel electrophoresis (SDS-PAGE). Proteins were immunoblotted with anti-strep mAb (DENVc; 1:500, Sigma Aldrich) and LRRK2 was detected with a pAb (1:1000, Cell Signalling Technology). The results are shown in FIG. 1.

As shown in FIG. 1 the DENV capsid interacts with LRRK2 when both proteins are expressed exogenously in 293T cells.

LRRK2 Kinase Inhibitor IN-1 Inhibits DENV Lifecycle.

A549 cells were preincubated with 1 μM of the LRRK2 kinase inhibitor IN-1 (cat. no. 4273, Tocris Bioscience (also referred to herein as Compound 1)), 1 μM LRRK2 inhibitor III (cat. no. 438195, EMD Millipore (also referred to herein as Compound 5)), or DMSO control. Cells were then infected with serial dilutions of DENV-2 (16681) for 2 hours in the continued presence of the indicated inhibitor. Infection media was removed and replaced with DMEM+0.8% methylcellulose containing the indicated inhibitor. Cells were fixed with 2% paraformaldehyde 48 hours post-infection, permeabilized, and stained for DENV E protein (4G2, Biomatik LLC, AlexaFluor 488 secondary). Viral plaque formation was quantified by IF microscopy. Data are represented as % infection in the experimental wells compared to the DMSO control. ***, p>0.001. The data are shown in FIG. 2A.

Figure 2A:
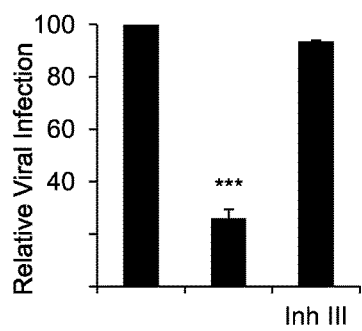
FIG. 2A-2C depict inhibition of DENV lifecycle with an LRRK2 inhibitor.

As shown in FIG. 2A, LRRK2 inhibitor IN-1 significantly inhibits viral infection.

A549 cells were pretreated with 1 μM of either IN-1, LRRK2 inhibitor III, or DMSO as a control for 2 hours before infection with DENV-2 (multiplicity of infection (MOI) ~1). Infection media was replaced with regular media containing the indicated inhibitors and incubated for an additional 48 hours. Cellular RNA was then extracted, purified, and relative DENV RNA was determined in each condition by RT-PCR. Data presented as DENV RNA copies normalized to a reference gene (18s) and subsequently compared to dimethyl sulfoxide (DMSO) control. The data are shown in FIG. 2B.

Figure 2B:
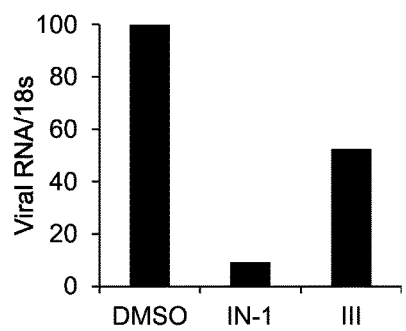

As shown in FIG. 2B, LRRK2 inhibitor IN-1 reduced viral genome abundance.

A549 cells were plated and incubated in the presence of IN-1 or DMSO control for 48 hours. An MTT (3-(4,5-dimethylthiazol-2-yl)-2,5-diphenyltetrazolium bromide) assay was then performed as per the manufacturers protocol (ATCC). The data are shown in FIG. 2C.

Figure 2C:
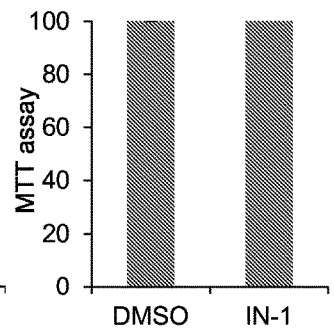

As shown in FIG. 2C, IN-1 is not cytotoxic to cells.

LRRK2 Depletion Inhibits the DENV Lifecycle.

A549 cells were individually transduced with four populations of LRRK2 targeting shRNAs and selected with puromycin for 24 hours. After selection, cellular RNA was extracted, purified, and LRRK2 expression level was determined by RT-PCR (left). Selected cells were also infected with DENV (16681) at a multiplicity of infection (MOI) of 1. DENV RNA was extracted, purified, and relative genome abundance was determined by RT-PCR (right). Data are presented as DENV genome abundance in the experimental wells compared to genome abundance in the scramble control well. The data are shown in FIG. 3.

Figure 3:
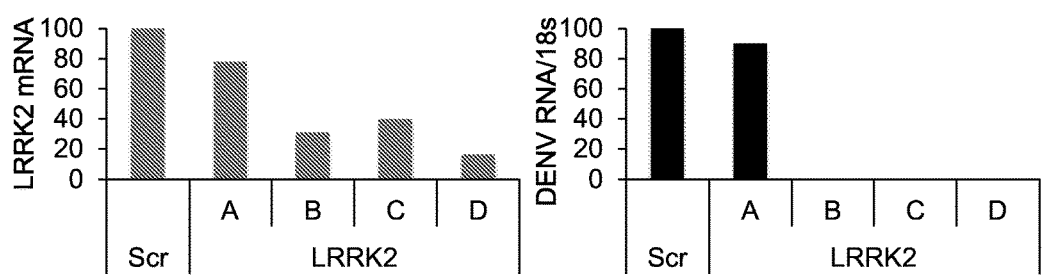
FIG. 3 depicts the effect of LRRK2 depletion on the DENV lifecycle.

As shown in FIG. 3, depletion of endogenous LRRK2 from A549 cells significantly inhibited DENV genome accumulation.

DENV Replication in iMPC-Heps is Ablated by IN-1.

Human hepatocytes were derived from fibroblasts as described in Zhu et al. ((2014) Nature 508:93). Induced multipotent progenitor cells (iMPC) were generated from human fibroblasts; and the iMPCs were used to generate hepatocytes. The hepatocytes thus generated are referred to as iMPC-HEPs. These hepatocytes were infected with DENV-2 (16681) and incubated for 48 hours. Cells were then fixed (2% paraformaldehyde) and stained for DENV capsid (4G2, Biomatik LLC, AlexaFluor 488 secondary) or human albumin (A80-129A, Bethyl, AlexaFluor 594 secondary). The data are shown in FIG. 4A.

Figure 4A:
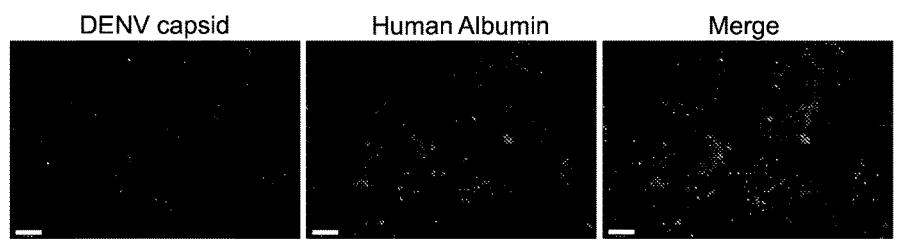
FIG. 4A-4B depict the effect of an LRRK2 inhibitor on DEVN replication in iMPC-Hepatocytes (iMPC-Heps).

As shown in FIG. 4A, DENV established a robust infection in iMPC-HEPs.

iMPC-Heps were treated with the indicated concentration of the LRRK2 kinase inhibitor IN-1 (cat. no. 4273, Tocris Bioscience) for 2 hours and subsequently infected with DENV-2 (16681). Virus was removed 2 hours post-infection and cells were incubated for 48 hours with the indicated concentration of IN-1. Viral RNA was extracted, purified, and viral RNA abundance was determined by RT-PCR. The data are shown in FIG. 4B.

Figure 4B:
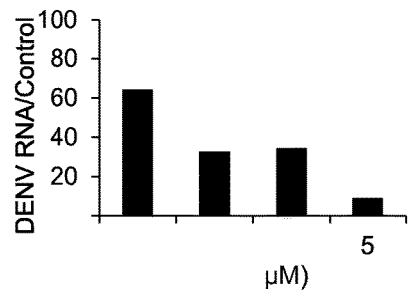

As shown in FIG. 4B, incubation of human hepatocytes with the LRRK2 kinase inhibitor IN-1 significantly reduced RNA replication in a dose-dependent manner. This indicates that LRRK2 inhibition is a potential therapeutic target for DENV infection by demonstrating efficacy in a model system using physiologically relevant primary cells.

Example 2: Inhibiting DENV with an Inhibitor of ARFGAP1

Leucine-rich repeat kinase 2 (LRRK2) is a large protein containing multiple domains, including a kinase domain and a GTPase domain. ADP ribosylation factor GTPase activating protein 1 (ARFGAP1) is a GTPase activating protein (GAP) for LRRK2. ARFGAP1 binds to LRRK2 and increases its GTPase activity. Furthermore, LRRK2 phosphorylates ARFGAP1 and inhibits its GAP activity, thus revealing the reciprocal regulation between these two proteins. It was hypothesized that both LRRK2 and ARFGAP1 play critical roles in the DENV life cycle.

A competitive inhibitor of ARFGAP1, QS 11, was used to show that ARFGAP1 is required for efficient DENV replication. Human hepatoma Huh7 cells were infected with DENV (MOI of 0.5) and treated with increasing concentrations of QS 11. Viral RNA synthesis, DENV capsid protein levels, and infectious virion production were measured at 24 hours post-infection. As shown in FIG. 6A-6C, QS 11 reduced viral RNA synthesis (FIG. 6A), DENV capsid protein levels (FIG. 6B), and infectious virion production (FIG. 6C).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method of treating a Dengue virus infection in an individual, the method comprising administering to the individual an effective amount of a leucine-rich repeat kinase 2 (LRRK2) inhibitor, wherein the LRRK2 inhibitor is Compound 1:

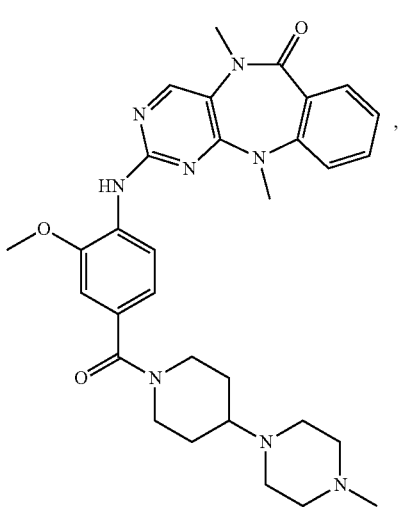

Compound 1

Compound 1, or a pharmaceutically acceptable salt thereof.

2. The method of claim 1, wherein the individual has been diagnosed as having a Dengue virus infection.

3. The method of claim 1, wherein the LRRK2 inhibitor is administered at a dose of from about 1 mg to about 100 mg per day.

4. The method of claim 1, wherein the LRRK2 inhibitor is administered at a dose of from about 10 mg to about 50 mg per day.

5. The method of claim 1, wherein the LRRK2 inhibitor is administered in an amount of from about 0.001 mg/kg/day to about 500 mg/kg/day.

6. The method of claim 1, wherein the LRRK2 inhibitor is administered orally.

7. The method of claim 1, wherein the LRRK2 inhibitor is administered intravenously.

8. The method of claim 1, wherein the LRRK2 inhibitor is administered subcutaneously.

9. The method of claim 1, wherein the LRRK2 inhibitor is administered intramuscularly.

10. The method of claim 1, wherein the individual is a human.

11. The method of claim 10, wherein said individual exhibits dengue hemorrhagic fever.

12. The method of claim 10, wherein said individual exhibits dengue shock syndrome.

13. The method of claim 1, wherein the LRRK2 inhibitor is Compound 1:

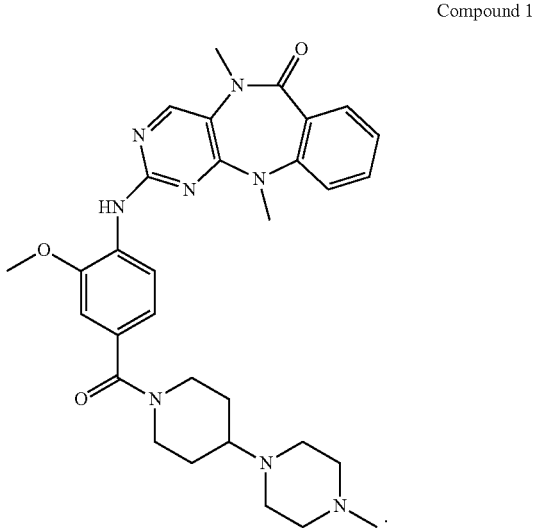 [SMILES: COc1cc(C(=O)N2CCC(N3CCN(C)CC3)CC2)ccc1Nc1ncc2c(n1)N(C)c1ccccc1C(=O)N2C]

Compound 1

* * * * *

SEQUENCE LISTING

```
<160> NUMBER OF SEQ ID NOS: 3

<210> SEQ ID NO 1
<211> LENGTH: 2527
<212> TYPE: PRT
<213> ORGANISM: Homo sapiens

<400> SEQUENCE: 1

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
```

```
            195                 200                 205
Leu Ser Ala Ser Thr Asn Phe Lys Asp Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
                260                 265                 270

Leu Leu His Arg Leu Thr Leu Gly Asn Phe Phe Asn Ile Leu Val Leu
            275                 280                 285

Asn Glu Val His Glu Phe Val Val Lys Ala Val Gln Gln Tyr Pro Glu
            290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
                340                 345                 350

Cys Tyr Lys Ala Leu Thr Trp His Arg Lys Asn Lys His Val Gln Glu
            355                 360                 365

Ala Ala Cys Trp Ala Leu Asn Asn Leu Leu Met Tyr Gln Asn Ser Leu
            370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
            435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
                500                 505                 510

Val Pro Gly Met Pro Glu Glu Ser Arg Glu Asp Thr Glu Phe His His
            515                 520                 525

Lys Leu Asn Met Val Lys Lys Gln Cys Phe Lys Asn Asp Ile His Lys
            530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
                580                 585                 590

Leu Gln Met Tyr Pro Asp Asp Gln Glu Ile Gln Cys Leu Gly Leu Ser
            595                 600                 605

Leu Ile Gly Tyr Leu Ile Thr Lys Lys Asn Val Phe Ile Gly Thr Gly
610                 615                 620
```

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
            645                 650                 655

Lys Leu Ser Ala Ser Phe Ser Lys Leu Leu Val His His Ser Phe Asp
                660                 665                 670

Leu Val Ile Phe His Gln Met Ser Ser Asn Ile Met Glu Gln Lys Asp
            675                 680                 685

Gln Gln Phe Leu Asn Leu Cys Cys Lys Cys Phe Ala Lys Val Ala Met
        690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu Ser Gln Lys Cys Cys Ile Ser Val
        995                 1000                1005

His Leu Glu His Leu Glu Lys Leu Glu Leu His Gln Asn Ala Leu
    1010                1015                1020

Thr Ser Phe Pro Gln Gln Leu Cys Glu Thr Leu Lys Ser Leu Thr
    1025                1030                1035

```
His Leu Asp Leu His Ser Asn Lys Phe Thr Ser Phe Pro Ser Tyr
    1040                1045                1050

Leu Leu Lys Met Ser Cys Ile Ala Asn Leu Asp Val Ser Arg Asn
    1055                1060                1065

Asp Ile Gly Pro Ser Val Val Leu Asp Pro Thr Val Lys Cys Pro
    1070                1075                1080

Thr Leu Lys Gln Phe Asn Leu Ser Tyr Asn Gln Leu Ser Phe Val
    1085                1090                1095

Pro Glu Asn Leu Thr Asp Val Val Glu Lys Leu Glu Gln Leu Ile
    1100                1105                1110

Leu Glu Gly Asn Lys Ile Ser Gly Ile Cys Ser Pro Leu Arg Leu
    1115                1120                1125

Lys Glu Leu Lys Ile Leu Asn Leu Ser Lys Asn His Ile Ser Ser
    1130                1135                1140

Leu Ser Glu Asn Phe Leu Glu Ala Cys Pro Lys Val Glu Ser Phe
    1145                1150                1155

Ser Ala Arg Met Asn Phe Leu Ala Ala Met Pro Phe Leu Pro Pro
    1160                1165                1170

Ser Met Thr Ile Leu Lys Leu Ser Gln Asn Lys Phe Ser Cys Ile
    1175                1180                1185

Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230

Ile Leu Asp Leu Ser Glu Lys Ala Tyr Leu Trp Ser Arg Val Glu
    1235                1240                1245

Lys Leu His Leu Ser His Asn Lys Leu Lys Glu Ile Pro Pro Glu
    1250                1255                1260

Ile Gly Cys Leu Glu Asn Leu Thr Ser Leu Asp Val Ser Tyr Asn
    1265                1270                1275

Leu Glu Leu Arg Ser Phe Pro Asn Glu Met Gly Lys Leu Ser Lys
    1280                1285                1290

Ile Trp Asp Leu Pro Leu Asp Glu Leu His Leu Asn Phe Asp Phe
    1295                1300                1305

Lys His Ile Gly Cys Lys Ala Lys Asp Ile Ile Arg Phe Leu Gln
    1310                1315                1320

Gln Arg Leu Lys Lys Ala Val Pro Tyr Asn Arg Met Lys Leu Met
    1325                1330                1335

Ile Val Gly Asn Thr Gly Ser Gly Lys Thr Thr Leu Leu Gln Gln
    1340                1345                1350

Leu Met Lys Thr Lys Lys Ser Asp Leu Gly Met Gln Ser Ala Thr
    1355                1360                1365

Val Gly Ile Asp Val Lys Asp Trp Pro Ile Gln Ile Arg Asp Lys
    1370                1375                1380

Arg Lys Arg Asp Leu Val Leu Asn Val Trp Asp Phe Ala Gly Arg
    1385                1390                1395

Glu Glu Phe Tyr Ser Thr His Pro His Phe Met Thr Gln Arg Ala
    1400                1405                1410

Leu Tyr Leu Ala Val Tyr Asp Leu Ser Lys Gly Gln Ala Glu Val
    1415                1420                1425

Asp Ala Met Lys Pro Trp Leu Phe Asn Ile Lys Ala Arg Ala Ser
```

-continued

```
            1430                1435                1440
Ser Ser Pro Val Ile Leu Val Gly Thr His Leu Asp Val Ser Asp
    1445                1450                1455
Glu Lys Gln Arg Lys Ala Cys Met Ser Lys Ile Thr Lys Glu Leu
    1460                1465                1470
Leu Asn Lys Arg Gly Phe Pro Ala Ile Arg Asp Tyr His Phe Val
    1475                1480                1485
Asn Ala Thr Glu Glu Ser Asp Ala Leu Ala Lys Leu Arg Lys Thr
    1490                1495                1500
Ile Ile Asn Glu Ser Leu Asn Phe Lys Ile Arg Asp Gln Leu Val
    1505                1510                1515
Val Gly Gln Leu Ile Pro Asp Cys Tyr Val Glu Leu Glu Lys Ile
    1520                1525                1530
Ile Leu Ser Glu Arg Lys Asn Val Pro Ile Glu Phe Pro Val Ile
    1535                1540                1545
Asp Arg Lys Arg Leu Leu Gln Leu Val Arg Glu Asn Gln Leu Gln
    1550                1555                1560
Leu Asp Glu Asn Glu Leu Pro His Ala Val His Phe Leu Asn Glu
    1565                1570                1575
Ser Gly Val Leu Leu His Phe Gln Asp Pro Ala Leu Gln Leu Ser
    1580                1585                1590
Asp Leu Tyr Phe Val Glu Pro Lys Trp Leu Cys Lys Ile Met Ala
    1595                1600                1605
Gln Ile Leu Thr Val Lys Val Glu Gly Cys Pro Lys His Pro Lys
    1610                1615                1620
Gly Ile Ile Ser Arg Arg Asp Val Glu Lys Phe Leu Ser Lys Lys
    1625                1630                1635
Arg Lys Phe Pro Lys Asn Tyr Met Ser Gln Tyr Phe Lys Leu Leu
    1640                1645                1650
Glu Lys Phe Gln Ile Ala Leu Pro Ile Gly Glu Glu Tyr Leu Leu
    1655                1660                1665
Val Pro Ser Ser Leu Ser Asp His Arg Pro Val Ile Glu Leu Pro
    1670                1675                1680
His Cys Glu Asn Ser Glu Ile Ile Ile Arg Leu Tyr Glu Met Pro
    1685                1690                1695
Tyr Phe Pro Met Gly Phe Trp Ser Arg Leu Ile Asn Arg Leu Leu
    1700                1705                1710
Glu Ile Ser Pro Tyr Met Leu Ser Gly Arg Glu Arg Ala Leu Arg
    1715                1720                1725
Pro Asn Arg Met Tyr Trp Arg Gln Gly Ile Tyr Leu Asn Trp Ser
    1730                1735                1740
Pro Glu Ala Tyr Cys Leu Val Gly Ser Glu Val Leu Asp Asn His
    1745                1750                1755
Pro Glu Ser Phe Leu Lys Ile Thr Val Pro Ser Cys Arg Lys Gly
    1760                1765                1770
Cys Ile Leu Leu Gly Gln Val Val Asp His Ile Asp Ser Leu Met
    1775                1780                1785
Glu Glu Trp Phe Pro Gly Leu Leu Glu Ile Asp Ile Cys Gly Glu
    1790                1795                1800
Gly Glu Thr Leu Leu Lys Lys Trp Ala Leu Tyr Ser Phe Asn Asp
    1805                1810                1815
Gly Glu Glu His Gln Lys Ile Leu Leu Asp Asp Leu Met Lys Lys
    1820                1825                1830
```

```
Ala Glu Glu Gly Asp Leu Leu Val Asn Pro Asp Gln Pro Arg Leu
1835                 1840                1845

Thr Ile Pro Ile Ser Gln Ile Ala Pro Asp Leu Ile Leu Ala Asp
1850                 1855                1860

Leu Pro Arg Asn Ile Met Leu Asn Asn Asp Glu Leu Glu Phe Glu
1865                 1870                1875

Gln Ala Pro Glu Phe Leu Leu Gly Asp Gly Ser Phe Gly Ser Val
1880                 1885                1890

Tyr Arg Ala Ala Tyr Glu Gly Glu Val Ala Val Lys Ile Phe
1895                 1900                1905

Asn Lys His Thr Ser Leu Arg Leu Leu Arg Gln Glu Leu Val Val
1910                 1915                1920

Leu Cys His Leu His His Pro Ser Leu Ile Ser Leu Leu Ala Ala
1925                 1930                1935

Gly Ile Arg Pro Arg Met Leu Val Met Glu Leu Ala Ser Lys Gly
1940                 1945                1950

Ser Leu Asp Arg Leu Leu Gln Gln Asp Lys Ala Ser Leu Thr Arg
1955                 1960                1965

Thr Leu Gln His Arg Ile Ala Leu His Val Ala Asp Gly Leu Arg
1970                 1975                1980

Tyr Leu His Ser Ala Met Ile Ile Tyr Arg Asp Leu Lys Pro His
1985                 1990                1995

Asn Val Leu Leu Phe Thr Leu Tyr Pro Asn Ala Ala Ile Ile Ala
2000                 2005                2010

Lys Ile Ala Asp Tyr Gly Ile Ala Gln Tyr Cys Cys Arg Met Gly
2015                 2020                2025

Ile Lys Thr Ser Glu Gly Thr Pro Gly Phe Arg Ala Pro Glu Val
2030                 2035                2040

Ala Arg Gly Asn Val Ile Tyr Asn Gln Gln Ala Asp Val Tyr Ser
2045                 2050                2055

Phe Gly Leu Leu Leu Tyr Asp Ile Leu Thr Thr Gly Gly Arg Ile
2060                 2065                2070

Val Glu Gly Leu Lys Phe Pro Asn Glu Phe Asp Glu Leu Glu Ile
2075                 2080                2085

Gln Gly Lys Leu Pro Asp Pro Val Lys Glu Tyr Gly Cys Ala Pro
2090                 2095                2100

Trp Pro Met Val Glu Lys Leu Ile Lys Gln Cys Leu Lys Glu Asn
2105                 2110                2115

Pro Gln Glu Arg Pro Thr Ser Ala Gln Val Phe Asp Ile Leu Asn
2120                 2125                2130

Ser Ala Glu Leu Val Cys Leu Thr Arg Arg Ile Leu Leu Pro Lys
2135                 2140                2145

Asn Val Ile Val Glu Cys Met Val Ala Thr His His Asn Ser Arg
2150                 2155                2160

Asn Ala Ser Ile Trp Leu Gly Cys Gly His Thr Asp Arg Gly Gln
2165                 2170                2175

Leu Ser Phe Leu Asp Leu Asn Thr Glu Gly Tyr Thr Ser Glu Glu
2180                 2185                2190

Val Ala Asp Ser Arg Ile Leu Cys Leu Ala Leu Val His Leu Pro
2195                 2200                2205

Val Glu Lys Glu Ser Trp Ile Val Ser Gly Thr Gln Ser Gly Thr
2210                 2215                2220
```

-continued

```
Leu Leu Val Ile Asn Thr Glu Asp Gly Lys Lys Arg His Thr Leu
2225                2230                2235

Glu Lys Met Thr Asp Ser Val Thr Cys Leu Tyr Cys Asn Ser Phe
2240                2245                2250

Ser Lys Gln Ser Lys Gln Lys Asn Phe Leu Leu Val Gly Thr Ala
    2255                2260                2265

Asp Gly Lys Leu Ala Ile Phe Glu Asp Lys Thr Val Lys Leu Lys
    2270                2275                2280

Gly Ala Ala Pro Leu Lys Ile Leu Asn Ile Gly Asn Val Ser Thr
    2285                2290                2295

Pro Leu Met Cys Leu Ser Glu Ser Thr Asn Ser Thr Glu Arg Asn
    2300                2305                2310

Val Met Trp Gly Gly Cys Gly Thr Lys Ile Phe Ser Phe Ser Asn
    2315                2320                2325

Asp Phe Thr Ile Gln Lys Leu Ile Glu Thr Arg Thr Ser Gln Leu
    2330                2335                2340

Phe Ser Tyr Ala Ala Phe Ser Asp Ser Asn Ile Ile Thr Val Val
    2345                2350                2355

Val Asp Thr Ala Leu Tyr Ile Ala Lys Gln Asn Ser Pro Val Val
    2360                2365                2370

Glu Val Trp Asp Lys Lys Thr Glu Lys Leu Cys Gly Leu Ile Asp
    2375                2380                2385

Cys Val His Phe Leu Arg Glu Val Met Val Lys Glu Asn Lys Glu
    2390                2395                2400

Ser Lys His Lys Met Ser Tyr Ser Gly Arg Val Lys Thr Leu Cys
    2405                2410                2415

Leu Gln Lys Asn Thr Ala Leu Trp Ile Gly Thr Gly Gly Gly His
    2420                2425                2430

Ile Leu Leu Leu Asp Leu Ser Thr Arg Arg Leu Ile Arg Val Ile
    2435                2440                2445

Tyr Asn Phe Cys Asn Ser Val Arg Val Met Met Thr Ala Gln Leu
    2450                2455                2460

Gly Ser Leu Lys Asn Val Met Leu Val Leu Gly Tyr Asn Arg Lys
    2465                2470                2475

Asn Thr Glu Gly Thr Gln Lys Gln Lys Glu Ile Gln Ser Cys Leu
    2480                2485                2490

Thr Val Trp Asp Ile Asn Leu Pro His Glu Val Gln Asn Leu Glu
    2495                2500                2505

Lys His Ile Glu Val Arg Lys Glu Leu Ala Glu Lys Met Arg Arg
    2510                2515                2520

Thr Ser Val Glu
    2525

<210> SEQ ID NO 2
<211> LENGTH: 516
<212> TYPE: PRT
<213> ORGANISM: Homo sapiens

<400> SEQUENCE: 2

Met Gly Asp Pro Ser Lys Gln Asp Ile Leu Thr Ile Phe Lys Arg Leu
1               5                   10                  15

Arg Ser Val Pro Thr Asn Lys Val Cys Phe Asp Cys Gly Ala Lys Asn
                20                  25                  30

Pro Ser Trp Ala Ser Ile Thr Tyr Gly Val Phe Leu Cys Ile Asp Cys
            35                  40                  45
```

-continued

```
Ser Gly Ser His Arg Ser Leu Gly Val His Leu Ser Phe Ile Arg Ser
     50                   55                  60

Thr Glu Leu Asp Ser Asn Trp Ser Trp Phe Gln Leu Arg Cys Met Gln
65                   70                  75                  80

Val Gly Gly Asn Ala Ser Ala Ser Ser Phe Phe His Gln His Gly Cys
                         85                  90                  95

Ser Thr Asn Asp Thr Asn Ala Lys Tyr Asn Ser Arg Ala Ala Gln Leu
                100                 105                 110

Tyr Arg Glu Lys Ile Lys Ser Leu Ala Ser Gln Ala Thr Arg Lys His
            115                 120                 125

Gly Thr Asp Leu Trp Leu Asp Ser Cys Val Val Pro Pro Leu Ser Pro
    130                 135                 140

Pro Pro Lys Glu Glu Asp Phe Phe Ala Ser His Val Ser Pro Glu Val
145                 150                 155                 160

Ser Asp Thr Ala Trp Ala Ser Ala Ile Ala Glu Pro Ser Ser Leu Thr
                    165                 170                 175

Ser Arg Pro Val Glu Thr Thr Leu Glu Asn Asn Glu Gly Gly Gln Glu
                180                 185                 190

Gln Gly Pro Ser Val Glu Gly Leu Asn Val Pro Thr Lys Ala Thr Leu
            195                 200                 205

Glu Val Ser Ser Ile Ile Lys Lys Lys Pro Asn Gln Ala Lys Lys Gly
    210                 215                 220

Leu Gly Ala Lys Lys Gly Ser Leu Gly Ala Gln Lys Leu Ala Asn Thr
225                 230                 235                 240

Cys Phe Asn Glu Ile Glu Lys Gln Ala Gln Ala Asp Lys Met Lys
                    245                 250                 255

Glu Gln Glu Asp Leu Ala Lys Val Val Ser Lys Glu Glu Ser Ile Val
                260                 265                 270

Ser Ser Leu Arg Leu Ala Tyr Lys Asp Leu Glu Ile Gln Met Lys Lys
            275                 280                 285

Asp Glu Lys Met Asn Ile Ser Gly Lys Lys Asn Val Asp Ser Asp Arg
    290                 295                 300

Leu Gly Met Gly Phe Gly Asn Cys Arg Ser Val Ile Ser His Ser Val
305                 310                 315                 320

Thr Ser Asp Met Gln Thr Ile Glu Gln Glu Ser Pro Ile Met Ala Lys
                    325                 330                 335

Pro Arg Lys Lys Tyr Asn Asp Asp Ser Asp Asp Ser Tyr Phe Thr Ser
                340                 345                 350

Ser Ser Arg Tyr Phe Asp Glu Pro Val Glu Leu Arg Ser Ser Ser Phe
            355                 360                 365

Ser Ser Trp Asp Asp Ser Asp Ser Tyr Trp Lys Lys Glu Thr Ser
    370                 375                 380

Lys Asp Thr Glu Thr Val Leu Lys Thr Thr Gly Tyr Ser Asp Arg Pro
385                 390                 395                 400

Thr Ala Arg Arg Lys Pro Asp Tyr Glu Pro Val Glu Asn Thr Asp Glu
                    405                 410                 415

Ala Gln Lys Lys Phe Gly Asn Val Lys Ala Ile Ser Ser Asp Met Tyr
                420                 425                 430

Phe Gly Arg Gln Ser Gln Ala Asp Tyr Glu Thr Arg Ala Arg Leu Glu
            435                 440                 445

Arg Leu Ser Ala Ser Ser Ile Ser Ser Ala Asp Leu Phe Glu Glu
    450                 455                 460
```

```
Pro Arg Lys Gln Pro Ala Gly Asn Tyr Ser Leu Ser Ser Val Leu Pro
465                 470                 475                 480

Asn Ala Pro Asp Met Ala Gln Phe Lys Gln Gly Val Arg Ser Val Ala
                485                 490                 495

Gly Lys Leu Ser Val Phe Ala Asn Gly Val Val Thr Ser Ile Gln Asp
            500                 505                 510

Arg Tyr Gly Ser
        515

<210> SEQ ID NO 3
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 3

Arg Leu Gly Arg Asp Lys Tyr Lys Thr Leu Arg Gln Ile Arg Gln
1               5                   10                  15
```